US012576128B2

(12) United States Patent
Bucci et al.

(10) Patent No.: US 12,576,128 B2
(45) Date of Patent: Mar. 17, 2026

(54) GENETICALLY ENGINEERED MICROORGANISMS AND METHODS OF USE

(71) Applicant: University of Massachusetts, Boston, MA (US)

(72) Inventors: Vanni Bucci, Brookline, MA (US); Benedikt Mortzfeld, Cumberland, RI (US); Jacob Palmer, Oxford (GB)

(73) Assignee: University of Massachusetts, Westborough, MA (US)

( * ) Notice: Subject to any disclaimer, the term of this patent is extended or adjusted under 35 U.S.C. 154(b) by 1121 days.

(21) Appl. No.: 17/608,053

(22) PCT Filed: May 1, 2020

(86) PCT No.: PCT/US2020/031182
§ 371 (c)(1),
(2) Date: Nov. 1, 2021

(87) PCT Pub. No.: WO2020/227155
PCT Pub. Date: Nov. 12, 2020

(65) Prior Publication Data
US 2022/0218787 A1      Jul. 14, 2022

Related U.S. Application Data

(60) Provisional application No. 62/942,537, filed on Dec. 2, 2019, provisional application No. 62/843,149, filed on May 3, 2019.

(51) Int. Cl.
*A61K 38/16* (2006.01)
*A61K 35/741* (2015.01)
(Continued)

(52) U.S. Cl.
CPC .......... *A61K 38/164* (2013.01); *A61K 35/741* (2013.01); *A61P 31/04* (2018.01);
(Continued)

(58) Field of Classification Search
None
See application file for complete search history.

(56) References Cited

U.S. PATENT DOCUMENTS 11,560,543 B2     1/2023   Bucci et al.
2006/0269988 A1   11/2006  Royer et al.
(Continued)

FOREIGN PATENT DOCUMENTS

WO     WO 2010/025267     3/2010
WO     WO 2016/072936     5/2016
(Continued)

OTHER PUBLICATIONS

Azpiroz et al., "Microcin H47 system: an *Escherichia coli* small genomic island with novel features," PLoS One, Oct. 11, 2011, 6(10):e26179, 7 pages.
(Continued)

*Primary Examiner* — Manjunath N Rao
*Assistant Examiner* — Qing Xu
(74) *Attorney, Agent, or Firm* — Fish & Richardson P.C.

(57) ABSTRACT
This disclosure relates to genetically engineered microorganisms for treating or reducing the risk of bacterial infections or dysbiosis, and further discloses methods of making and using such microorganisms.

20 Claims, 3 Drawing Sheets
Specification includes a Sequence Listing.

(51) Int. Cl.
    *A61P 31/04*     (2006.01)
    *C12N 1/20*     (2006.01)
    *C12N 15/63*     (2006.01)
    *C12N 15/70*     (2006.01)
    *C12P 21/02*     (2006.01)

(52) U.S. Cl.
    CPC ............. *C12N 1/20* (2013.01); *C12N 15/635*
       (2013.01); *C12N 15/70* (2013.01); *C12P 21/02*
         (2013.01); *C12N 2510/00* (2013.01); *C12N*
           *2800/101* (2013.01); *C12N 2830/002* (2013.01)

(56)           References Cited

U.S. PATENT DOCUMENTS

| | | | |
|---|---|---|---|
| 2015/0209393 A1 | 7/2015 | Wook et al. | |
| 2018/0099013 A1* | 4/2018 | Borody ................. | A61K 35/74 |
| 2020/0270569 A1 | 8/2020 | Bucci et al. | |
| 2023/0126514 A1 | 4/2023 | Bucci et al. | |

FOREIGN PATENT DOCUMENTS

| | | |
|---|---|---|
| WO | WO 2016/210373 | 12/2016 |
| WO | WO 2018/237198 | 12/2018 |
| WO | WO 2019/055781 | 3/2019 |

OTHER PUBLICATIONS

Azpiroz et al., "Microcins and urovirulence in *Escherichia coli*. Microbial pathogenesis," Nov. 2009. 47(5):274-80.

Bayro et al., "Structure of antibacterial peptide microcin J25: a 21-residue lariat protoknot," Journal of the American Chemical Society, Oct. 13, 2003, 125(41): 12382-3.

Bucci et al., "The evolution of bacteriocin production in bacterial biofilms," The American Naturalist, Dec. 1, 2011, 178(6):E162-73.

Chatham-Stephens et al., "Emergence of extensively drug-resistant *Salmonella Typhi* infections among travelers to or from Pakistan-United States, 2016-2018," Morbidity and Mortality Weekly Report, Jan. 11, 2019, 68(1):11, 5 pages.

Daeffler et al., "Engineering bacterial thiosulfate and tetrathionate sensors for detecting gut inflammation," Molecular Systems Biology, Apr. 2017, 13(4):923, 13 pages.

David et al., "Epidemic of carbapenem-resistant Klebsiella pneumoniae in Europe is driven by nosocomial spread," Nature Microbiology, Nov. 2019, 4(11):1919-29.

Delgado et al., "YojI of *Escherichia coli* functions as a microcin J25 efflux pump," Journal of Bacteriology, May 15, 2005, 187(10):3465-70.

EP European Search Report in European Appln. No. 18856596.4, dated Aug. 7, 2020, 17 pages.

EP Extended European Search Report in European Appln. No. 18856596.4, dated Nov. 10, 2020, 15 pages.

Geldart et al., "pMPES: a modular peptide expression system for the delivery of antimicrobial peptides to the site of gastrointestinal infections using probiotics," Pharmaceuticals, Dec. 2016, 9(4):60, 16 pages.

Gibson et al., "Enzymatic assembly of DNA molecules up to several hundred kilobases," Nature Methods, May 2009, 6(5):343-5.

Landry et al., "Engineering diagnostic and therapeutic gut bacteria," Microbiology Spectrum, Oct. 2017, 5(5), 22 pages.

Medina et al., "Tackling threats and future problems of multidrug-resistant bacteria," How To Overcome the Antibiotic Crisis, 2016, 3-33.

Mercado et al., "The production in vivo of microcin E492 with antibacterial activity depends on salmochelin and EntF," Journal of Bacteriology, Aug. 1, 2008, 190(15):5464-71.

Metelev et al., "Structure of microcin B-like compounds produced by Pseudomonas syringae and species specificity of their antibacterial action," Journal of Bacteriology, Sep. 15, 2013, 195(18):4129-37.

Nadell et al., "Cutting through the complexity of cell collectives. Proceedings of the Royal Society B: Biological Sciences," Mar. 22, 2013, 280, 11 pages.

Ng et al., "Microbiota-liberated host sugars facilitate post-antibiotic expansion of enteric pathogens," Nature, Oct. 2013, 502(7469):96-9.

Nolan et al., "Biosynthetic tailoring of microcin E492m: post-translational modification affords an antibacterial siderophore-peptide conjugate," Journal of the American Chemical Society, Nov. 21, 2007, 129(46):14336-47.

Nolan et al., "Investigations of the MceIJ-catalyzed post-translational modification of the microcin E492 C-terminus: linkage of ribosomal and nonribosomal peptides to form"trojan horse"antibiotics," Biochemistry, Sep. 2, 2008, 47(35):9289-99.

Palmer et al., "Engineered probiotic for the inhibition of *Salmonella* via tetrathionate-induced production of microcin H47," ACS Infectious Diseases, Jan. 12, 2018, 4(1):39-45.

Patzer et al., "The colicin G, H and X determinants encode microcins M and H47, which might utilize the catecholate siderophore receptors FepA, Cir, Fiu and IroN," Microbiology, Sep. 1, 2003, 149(9):2557-70.

PCT International Preliminary Report on Patentability in International Appln. No. PCT/US2018/051079, dated Mar. 17, 2020, 9 pages.

PCT International Preliminary Report on Patentability in International Appln. No. PCT/US2020/031182, dated Nov. 2, 2021, 6 pages.

PCT International Preliminary Report on Patentability in International Appln. No. PCT/US2021/019225, dated Feb. 3, 2022, 11 pages.

PCT International Search Report and Written Opinion in International Appln. No. PCT/U20S18/051079 dated Feb. 7, 2019, 13 pages.

PCT International Search Report and Written Opinion in International Appln. No. PCT/US2020/031182, dated Aug. 18, 2020, 9 pages.

PCT International Search Report and Written Opinion in International Appln. No. PCT/US2021/019225, dated Aug. 10, 2021, 11 pages.

Poey et al., "Comparative analysis of chromosome-encoded microcins," Antimicrobial Agents and Chemotherapy, Apr. 1, 2006, 50(4):1411-8.

Riglar et al., "Engineered bacteria can function in the mammalian gut long-term as live diagnostics of inflammation," Nature Biotechnology, Jul. 2017, 35(7):653-8.

Rodriguez et al., "The structural gene for microcin H47 encodes a peptide precursor with antibiotic activity," Antimicrobial Agents and Chemotherapy, Sep. 1, 1999, 43(9):2176-82.

Rojas et al., "Multidrug-Resistant Klebsiella pneumoniae ST307 in Traveler Returning from Puerto Rico to Dominican Republic," Emerging Infectious Diseases, Aug. 2019, 25(8):1583-5.

Sassone-Corsi et al.et al., MicrocIns Mediate Competition Among Enterobacteriaceae In the Inflamed Gut Naure; Dec. 8, 2016; vol. 540, 25 pages.

Winter et al., "Gut inflammation provides a respiratory electron acceptor for *Salmonella*," Nature, Sep. 2010, 467(7314):426-9.

Winter et al., "Host-derived nitrate boosts growth of *E. coli* in the inflamed gut," Science, Feb. 8, 2013, 339(6120):708-11, 5 pages.

Duquesne et al., "Microcins, gene-encoded antibacterial peptides from enterobacteria," Natural Product Reports, 2007, 24(4):708-34.

EP European Search Report in European Appln. No. 20802507.2, dated Jun. 15, 2022, 9 pages.

Fomenko et al., "Regulation of microcin C51 operon expression: the role of global regulators of transcription," Research in Microbiology, Jun. 1, 2001, 152(5):469-79.

Geldart et al., "pMPES: a modular peptide expression system for the delivery of antimicrobial peptides to the site of gastrointestinal infections using probiotics," Pharmaceuticals, Oct. 2, 2016, 9(4):60, 16 pages.

Mortzfeld et al., "Mccl47 selectively inhibits enteric bacteria and reduces carbapenem-resistant Klebsiella pneumoniae colonization in vivo when administered via an engineered live biotherapeutic," bioRxiv, Jan. 1, 2021, vol. 2021, 22 pages.

(56) References Cited

OTHER PUBLICATIONS

Poey et al., "Virulence profiles in uropathogenic *Escherichia coli* isolated from pregnant women and children with urinary tract abnormalities, " Microbial Pathogenesis, May 1, 2012, 52(5):292-301.

Vassiliadis et al., "Isolation and characterization of two members of the siderophore-microcin family, microcins M and H47," Antimicrobial Agents and Chemotherapy, Jan. 2010, 54(1):288-97.

Bantysh et al., "Enzymatic synthesis of bioinformatically predicted microcin C-like compounds encoded by diverse bacteria," Mbio, Jul. 2014, 5(3): 10, 11 pages.

EP Extended European Search Report in European Appln. No. 21760771.2, mailed on Mar. 14, 2024, 11 pages.

Gaggero et al., "Genetic analysis of microcin H47 antibiotic system," Journal of Bacteriology, Sep. 1993, 175(17):5420-7.

Palmer et al., "Microcin H47: A Class IIb microcin with potent activity against multidrug resistant Enterobacteriaceae," ACS Infectious Diseases, Feb. 2020, 6(4):672-9.

Thomas et al., "Siderophore peptide, a new type of post-translationally modified antibacterial peptide with potent activity," Journal of Biological Chemistry, Jul. 2004, 279(27):28233-42.

* cited by examiner

1

GENETICALLY ENGINEERED MICROORGANISMS AND METHODS OF USE

CLAIM OF PRIORITY

This application is a U.S. National Stage Application of International Application No. PCT/US2020/031182, filed on May 1, 2020, which claims the benefit of U.S. Provisional Patent Application Ser. No. 62/843,149, filed May 3, 2019 and U.S. Provisional Patent Application Ser. No. 62/942,537, filed Dec. 2, 2019. The entire contents of the foregoing applications are hereby incorporated by reference.

FEDERALLY SPONSORED RESEARCH OR DEVELOPMENT

This invention was made with Government support under Grant Nos. DBI1458347 and 1817342 awarded by National Science Foundation and Grant No. AI112985 awarded by the National Institutes of Health. The Government has certain rights to the invention.

SEQUENCE LISTING

This application contains a Sequence Listing that has been submitted electronically as an ASCII text file named Sequence Listing.txt. The ASCII text file, created on Oct. 21, 2021, is 44,492 kilobytes in size. The material in the ASCII text file is hereby incorporated by reference in its entirety.

TECHNICAL FIELD

This disclosure relates to genetically engineered microorganisms and methods of use.

BACKGROUND

Medical complications related to drug-resistant bacteria (bacteria that cannot be treated with currently available antibiotics), including those from members of the family Enterobacteriaceae, are a major issue in modern healthcare due to the increased morbidity, mortality, length of hospitalization and related healthcare costs. The CDC estimates that every year more than two million people acquire multi-drug-resistant bacterial infections, which result in over 23,000 directly-related deaths and several more lethal outcomes from associated complications. A 2014 report from the World Health Organization (WHO) found that all WHO surveyed regions are characterized by high-rates of multi-drug resistant microorganisms, which are responsible for common health care facility and community acquired urinary tract infections (UTIs), pneumonias and blood stream infections. Of particular gravity is the fact that WHO's surveillance data are showing that more than 50% of *Klebsiella* species-related infections in all WHO regions are resistant to third generation Cephalosporin, with a significant portion (>20%) also showing concurrent resistance to its only alternative, Carbapenem.

A recent report has estimated that the economic burden for society due to Carbapenem-Resistant Enterobacteriaceae (CRE) infections, which include CR *Klebsiella pneumoniae* (CRKp), CR *Klebsiella oxytoca* (CRKo), CR *Enterobacter cloaceae* (CREc), and *Enterobacter aerogenes* (CREa), ranges from $37,000 to $83,000 per infection. When considering an infection incidence range of 2.93-15 per 100,000 people in the USA (i.e. 9,418-48,213 infections), CRE infections are estimated to cost society anything in the order of $1-$2 billion every year and to cause the loss of up to 45,261 quality-adjusted life years. Thus, there is pressing need to develop novel therapeutics that selectively kill pathogenic bacteria, reduce infection rates (and duration of infection), and curb the emergence of new drug-resistance mechanisms.

SUMMARY

The present disclosure provides compositions of engineered microorganisms to produce microcin I47 and methods of treating bacterial infections, e.g., gram-negative bacterial infections, and dysbiosis. The disclosure further provides genetically engineered microorganisms that include a microcin operon and a controllable promoter for the microcin operon. In particular, the microcin operon includes mciI, mciA, mchC, mchD, mchE, and mchF genes. The controllable promoter controls a level of expression of the one or more microcin genes, thereby controlling the amount of microcin produced by the genetically engineered microorganism. Either or both of the microcin operon and the controllable promoter are heterologous to the microorganism.

In one aspect, the disclosure provides genetically engineered microorganisms capable of producing microcin I47, wherein the microorganism include a microcin operon, and a first controllable promoter for the microcin operon, wherein the microcin operon comprises microcin genes mciI, mciA, mchC, and mchD, wherein the first controllable promoter controls a level of expression of at least the one of the microcin genes, thereby controlling the amount of microcin produced by the genetically engineered microorganism, and wherein either or both of the microcin operon and the first controllable promoter are heterologous to the microorganism.

In some embodiments, the genetically engineered microorganism is a bacterium. In some embodiments, the genetically engineered microorganism is *Escherichia coli.*

In some embodiments, the microorganism further comprises a second microcin operon comprising microcin gene mchA and a second controllable promoter for the second microcin operon, wherein the second controllable promoter controls a level of expression of mchA, thereby controlling the amount of microcin produced by the genetically engineered microorganism.

In some embodiments, the second microcin operon further comprises microcin gene mchS4, microcin gebe mchS1, or both.

In some embodiments, the controllable promoter is a pJ23119 promoter.

In some embodiments, the first microcin operon further comprises microcin genes mchE and mchF.

In some embodiments, the first or the second microcin operon, or both the first and the second microcin operons and the first or second controllable promoter, or both the first and the second controllable promoters are in the genome of the microorganism.

In some embodiments, the first or the second microcin operon, or both the first and the second microcin operons, and the first or second controllable promoter, or both the first and the second controllable promoters are in a vector.

In some embodiments, the composition includes any one of the genetically engineered microorganisms described herein.

In some embodiments, the composition is packaged in a capsule for intestinal delivery.

In another aspect, the disclosure provides methods of treating intestinal dysbiosis, the methods including identifying a subject as having intestinal dysbiosis; and administering to the subject a therapeutically effective amount of a composition comprising any one of the genetically engineered microorganism described herein.

In some embodiments, the subject is a human and the composition is administered by endoscopy, enteroscopy, colonoscopy, a nasoduodenal catheter, enema, or by oral administration. In some embodiments, the composition is orally administered, optionally in a capsule.

In another aspect, the disclosure features methods of treating a bacterial infection, the methods including identifying a subject as having a bacterial infection; and administering to the subject a therapeutically effective amount of a composition comprising any one of the genetically engineered microorganisms described herein.

In some embodiments, the subject is a human and the composition is administered by endoscopy, enteroscopy, colonoscopy, a nasoduodenal catheter, enema, or by oral administration. In some embodiments, the composition is orally administered, optionally in a capsule. In some embodiments, the bacterial infection is a gram-negative bacterial infection. In some embodiments, the bacterial infection is carbapenem-resistant Enterobacteriaceae infection, *Campylobacter* infection, *E. coli* infection, *Salmonella* infection, *Shigella* infection and/or *Yersinia* infection.

Also provided herein are methods of reducing a risk of a bacterial infection, the method comprising: identifying a subject as having a risk of a bacterial infection; and administering to the subject a composition comprising any one of the genetically engineered microorganisms described herein.

In some embodiments, the subject is being administered one or more antibiotics. In some embodiments, the subject is a human and the composition is administered by endoscopy, enteroscopy, colonoscopy, a nasoduodenal catheter, enema, or by oral administration. In some embodiments, the composition is orally administered, optionally in a capsule.

This disclosure provides new *E. coli* single-strain probiotics that produce microcin MccI47. As described herein, in vitro experiments using both heterologous I47 production from a probiotic or purified I47 show that microcin I47 is especially capable in killing CR *K. pneumoniae*. The disclosure further provides plasmid-based systems capable of producing microcin I47 and provides the use of mature (post-translationally modified) microcin I47 delivered from a probiotic or in its purified form as new antibiotic to kill bacteria, e.g., *Klebsiella* species with a specific focus on drug-resistant *Klebsiella* species. Moreover, I47 is able to kill with different efficacy other Enterobacteriaceae including *Escherichia coli, Salmonella typhimurium, Salmonella typhi*, and *Shigella flexneri* as well as drug resistant strains of these species. Based on the results described herein, the overproduction vectors described herein result in strong signals of decolonization, which greatly opens the opportunities for engineered biotherapeutics aimed at eradication of multidrug resistant (MDR) enteric bacteria.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated herein by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
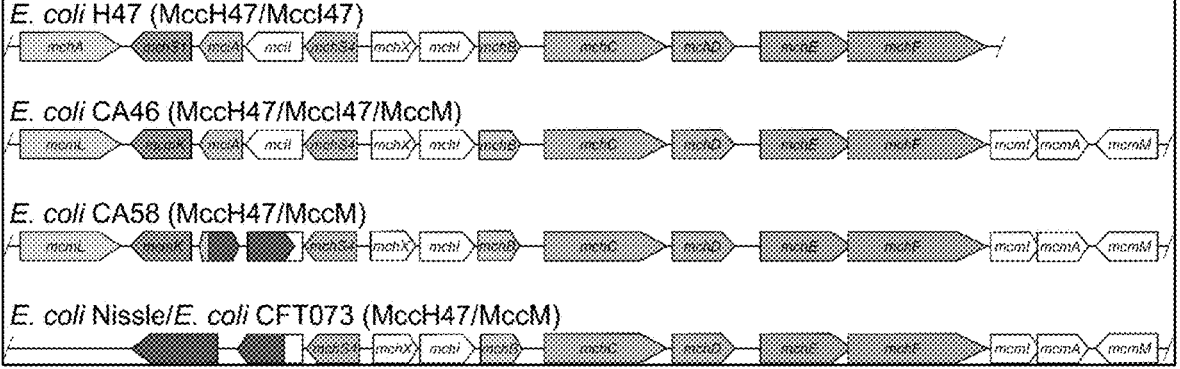
FIG. 1 is a diagram of select *E. coli* mch gene clusters. Genes sharing the same shade in the same strain are involved in similar function (e.g. mchEF-secretion). Genes sharing the same shade across different strains, and with different names indicate homologs (e.g. mchA-mcmL). Black coding regions indicate transposable elements. Microcins listed within parentheses denote presence of corresponding gene for microcin structural protein (mchB, mciA, mcmA).

Members of drug-resistant Enterobacteriaceae spp. include opportunistic pathogens (e.g., *Salmonella* spp.) are among the leading causes of morbidity and mortality worldwide. Overgrowth of these bacteria is considered a hallmark of intestinal dysbiosis. Some gut commensals produce microcins, small antimicrobial peptides, that inhibit growth of select pathogens. As described herein, select gut commensals can be genetically altered and used to effectively treat pathogenic bacteria infections and/or to limit the growth of pathogenic bacteria.

Delivery of rationally-designed combinations of gastrointestinal commensals has the benefit of ensuring CRE decolonization via a number of concurring mechanisms including competition for nutrient and space, production of antimicrobial molecules and immune-system stimulation. However, the cost of large-scale production of these consortia linearly scales with the number of employed species (1-2 months per strain based on work from our industrial partners), thus making the generation of consortia of dozens of strains a big and time-consuming endeavor. Recent work has shown that addition of single strains of microcinogenic intestinal residents (i.e. bacteria capable of secreting small antimicrobial peptides) can lead to the killing of pathogenic Gram-negative Enterobacteriaceae, and therefore could be used as novel live biotherapeutics. However, because native microcin production is performed by strains with unknown mammalian gut colonization capability, and is dependent on the conditions experienced in the intestine (e.g., iron limitation), this phenomenon is difficult to control and thus exploit for therapies.

We have built new prototypes of *E. coli* single-strain probiotics that produce a previously minimally-characterized microcin I47. Performing in vitro experiments using both heterologous I47 production from a probiotic or I47, purified for the first time by us, we observed that microcin I47 is especially capable in killing CR *K. pneumoniae*, suggesting that we have identified a novel molecule for the killing of this deadly pathogen.

The disclosure provides plasmid-based systems capable of producing microcin I47. The disclosure also provides the use of mature (post-translationally modified) microcin I47 delivered from a probiotic or in its purified form as new antibiotic to kill bacteria, e.g., *Klebsiella* species with a specific focus on drug-resistant *Klebsiella* species. Our data show that I47 can also kill with different efficacy other Enterobacteriaceae including *Escherichia coli, Salmonella typhimurium, Salmonella typhi*, and *Shigella flexneri*. Additionally, this disclosure provides genetically engineered probiotics capable of conditionally producing microcin I47.

Microcins

Microcins are low-molecular-weight antimicrobial peptides secreted by members of the Enterobacteriaceae family. They include, e.g., Class I microcins, Class IIa microcins, Class IIb microcins, and Class IIc microcins. Class I microcins have molecular masses <5 kDa, are post-translationally modified, and bind to a spectrum of targets. Class IIb microcins are relatively large (~5-10 kDa) polypeptides and feature a C-terminal siderophore post-translational modification. Class IIb microcins include, e.g., Microcin H47 (MccH47), MccE492, MccM, MccG492 and MccI47.

MccI47

Microcin I47 is a bactericidal antibiotic. Due to its size, it shares with other microcins the ability to pass through cellophane membranes. Microcin I47 has been reported to be produced by the MccH47 genetic system and detected in iron deprivation conditions (Azpiroz et al., 2011, *PLOS ONE* 6(10):e26179; Poey et al., 2006, *Antimicrob Agents Chemother* 50(4):1411-8).

Production and purification of microcin I47 can be conducted by any suitable method known in the art. In some embodiments, microcin I47 can be purified using an amylose resin column eluted with maltose. For example, cultures of *E. coli* producing microcin I47, e.g., *E. coli* NEB10β pHMT-I47, are grown under antibiotic selection (e.g., ampicillin and/or chloramphenicol), and in iron-limiting conditions, e.g., via the addition of 0.2 mM 2'2-dipyridyl, and induced, e.g., with isopropyl β-d-1-thiogalactopyranoside (IPTG). Cultures are grown for an additional time, e.g., 4 to 10 hours, e.g., 5 to 7 hours, post-induction, then pelleted and frozen overnight, e.g., at −20° C.

Cultures can then be thawed in cold water, sonicated, and the crude lysate is passed through a resin column, e.g., an amylose resin (New England Biolabs, Ipswich, MA) column, to capture maltose-binding protein (MBP) fusion proteins, then finally eluted, e.g., with maltose. Elution is performed by adding the elution buffer (e.g., 200 mM NaCl, 20 mM Tris-HCl, 10 mM maltose; pH 7.5).

The eluent can be concentrated, for example, using MilliporeSigma (Burlington, MA) MWCO 10,000 filters. The concentrated MBP-MccI47 is then digested by an endopeptidase, such as the Tobacco etch virus nuclear-inclusion-a endopeptidase (TEV) (New England Biolabs, Ipswich, MA), yielding a buffered solution of MccI47, TEV, and MBP. This solution can then be further purified, e.g., by subsequent rounds of resuspension with Ni-NTA agarose resin (Qiagen, Hilden, DE). Ni-NTA slurry can be pelleted by centrifugation and the supernatant can be removed by pipetting.

Genetic System for Producing MccI47 and MccH47

The genes required for production of MccI47 and MccH47 are clustered in a 10-kb DNA segment located in the *E. coli* chromosome and include the genes: mchA, mchB, mchC, mchD, mchE, mchF, mchI, mchX, mciA (formerly known as mchS2), mciI (formerly known as mchS3),mchS1, and mchS4. Three genes, mchA, mchC, and mchD, are devoted to mature microcin synthesis; whereas mciA and mciI encode for the precursor and the corresponding immunity peptide of MccI47 and mchB and mchI for the precursor and the corresponding immunity peptide of MccH47. Two further genes, mchE and mchF, are required for the secretion of the antibiotic into the extracellular medium.

Production of class IIb microcins is a process involving three main steps: synthesis of the precursor peptide, subsequent maturation of the molecule, and its final secretion. These microcin genes are described, e.g., in Vassiliadis et al. (2010) *Isolation and characterization of two members of the siderophore-microcin family, microcins M and H47, Antimicrobial agents and chemotherapy* 54.1:288-297, which is incorporated herein by reference in its entirety. The complexity of the MccI47 antibiotic system parallels that of other microcin systems, such as those of microcins B17 and C7. MccI47 maturation, in which mchA, mchC, and mchD gene products are known to be necessary, is believed to endow the antibiotic molecule with the ability to enter cells.

mchA gene sequence (SEQ ID NO: 1)

ATGCGAAAACGTATTCTTTTTATTGGCCCACCGCTGTACGGTTTGTTATA

CCCATTGATTTCTCTGGCTCAGGCCTTTCGTGTAATCGGACATGATGTAG

TAATTAGTAGTGCTGGCAAATTCGCGAATAAAGCAGCAGAAGCTGGACTG

GTTGTTTTTGATGCAGTTCCAGGTTTAGATTCAGAGGCTGGATATCGCCA

TCAGGAAGAGTTGAGGAAAAAAAGTAATATTATTGGTCATTTCTCTTTTT

TTAGCGATGAAATGGCAGATAACCTCATCGATTTTGCAGGAAAATGGAGG

CCAGATTTAATAGTCTATCCCCCGCTTGGTCCGGCAGGCCCATTGGTTGC

TGCTAAATATAGAATTCCTTCAGTGATGCTGGCTGTTGGATTCGCGCATA

CATCTGCCCATATTCAGATGTTAAACCGTTCTTTAAGCAATGCTTACAGG

CGGCATGGAGTCAGCGGTCCACTATGTGATTTAGCATGGATTGATGTTGC

TCCCCCAAGTATGAGCATTCTTAAAAATGCTGAAGAACCGGTTATCTCAA

TGAGATATATTCCTTATAACGGAGGTGCTGTAAAGGAAACATGGTGGGAC

AGGGATTCTGATCGAAACGTTTACTCATCAGCCTTGGCACTGTAAAACC

AATGGTTGATGGTCTGGAGCTGATTTCATGGGTTATGGATTCTGCAAATG

AAGTTGATGCTGATATCATTTTGCAACTTGCAATAAATGCTCGTACTGGA

-continued

```
TTACGAAAACTACCATCAAATGTACGTCTGGTTGACTGGATACCTATGGG

TGTATTCCTTAATGGAGCTGATGGATTTATTCATCATGGTGGCGCAGGTA

ATACCCTGACAGCGTTGTATAGTGGGATACCACAGATTGTGTTTGGCGAA

GGTGCAGATCGCTCTGTTAATGCAGAAATTGTTGCGATGCGTGGGTGTGG

GATTATTCCGGACAAGCATGGACTGACCAGTGATTTGGTAAATCGCCTGC

TTTATGATGATTCACTACGCTTCTGTTCAGATCAGGTAGCCGCTGAAATG

GCTGAACAACCCAGTCCTGCAGAGATCGCAGAGGTTTTGATGAGAAATT

AAAAAACAACGGGAAATAA.
``` mchC gene sequence:
```
                                    (SEQ ID NO: 2)
ATGAGTCATCAGTGTTCACTTTCTGAACTGAATGAAAACCTGGTGCCTTT

CACTGCCAGGCAGATCAAGTCCTCATTAATCTGGTGTGCAGAGGATGTCA

GAAATCCAGGCGAGCTGCAAAATGCCTGCAGTTATATTATCGATCCTGAC

AGTACGGCTTCTGCCAAAGTGTTCCATGCAGAGCGCTATGGTGGCAGTGG

TATTCAGCGTAATGGAGGTGGTGCACGTTGTGGGTTTGATGGTAACTACC

AGGTTAAAGGAATAGGAAGTAATCCGTTGGTTGGTGAAGGTACTGACGAA

CGTCATTCTAATGGTGCACTCGGCGCTGTTCATGCAATATATGAGGCTTT

GTGGGGAGAAGTACTGGCTCAAATATTACCTTATAGTGCTGTGCGGGTTC

GGGCGGTTTTACTTACAGATCTCTATACTGAAAAGGCATTTGAGCGCTCC

GGTATGAAATCACGAAGAGCCCTGTTGGTACGTGAGCCTGTTGTTCGCCC

GGCGCATTTTGAACGGGCACCATACTTCCAAGTAAAACCGGAGTATTCCA

GTCAGTTAATTCACGATGCCTGTCGGGTTAGATCTGTGATCCACAAGCTG

CCAGGATATCTACCTGTACCACCGGAAGAAATTGATGCTGAAGCACGAAC

TGATCCCCGGATTTATTGCATTGAGGGATTATGTGAACTGGCACGTCGTG

AGGCCTGGCAAATGGCATTTTGTCGAACACGTTTCCTGAGATTGACAACT

TCTCCTTCTAATATTGCAATGGATGGCAGATTAATGGATTTTAACGGACT

CAGTTGCTCGTTTCCGGGAGATTCCCCAGCTGATTTTGGGTATAAACTAA

GATTAGCTGAACTGGCAAAAGAACCGATGGTACTTATGCAAGGGCTGTCT

GATCTCTGCTTGTATATCGGAAAATATATGTTTGACCCTGACTTCACTCT

TGCAGCCCGTTTGAAGGTTGAGGAGATATTTCAGAAAACTTTTCATGAAG

CATGTTATTACTGTTATCTAGAACTGTTGGGTATTCCTGGAGAATTTATA

ACACAAAAAGAGATACCTGATATATTGAAACAACTGGTTAACAGTTTTGT

TGCATTACTCAATAAATACTGCGAGAAATCACATGCCCAAGATATTGTCA

ATCAGGATGGTTCACCATTGCAAAAGTTGGTTGTGACGCTAATCCATCAT

AGGCATAATCAAAAGCAGGCACTGAATAGTAGCATCAAGAATGATGTTTA

TTTCACCGTTGCACAACAGTGTTTTTCCCAGACTATCCACTGGCTGACGC

AAGGCAGTACCAGACGTCAGATAAATGCTTCATTACTCCTGAAAGAAATT

GAACATCATACCATGAAAAGGCTGCAACCCAGGGAAGAGCTGAGGAAAGA

GAATATGTGCGAAAAAATTGCCATCCTGCTGGATAATCATGGCGATGATC
```

-continued

```
CCCTTTTTTTACAAGAAGCAATTTCTGATATGAAAAATTTTATGCTTAAG

TTTTCCAGAGATGCATTTGGATATCTTGAACCGATAAGAAACACAGTGTA

A.
``` mchD gene sequence:
```
                                    (SEQ ID NO: 3)
ATGTCTTATATAAGGGAAACCATCAGAGGAAAAGATGAATGGACTGTTTA

TGAACAGATAGGTTTTGCGGTCAGTTGTATGCTCTACAATCGTAATTACA

GTCTGTATCCGGTGTTAACCATTCAATACTGGACTGAATATGCGATACAG

CATAATCAGATTAAATTCCTGTTTGATTCACGAGGTTTTCCACTGGCGTA

TATAACCTGGGCATATCTTGAGGCTGATACGGAAGCGCGCCTGCTCAGGG

ATCCAGAATTCAGGTTGCATCCGTCTGAATGGAATGAAGATGGAAGGATC

TGGATCCTGGATTTCTGTTGTAAACCAGGCTTTGGTCGAAAAGTTATTGA

CTATCTCATACAGCTTCAGCCATGGGGGGAAGGAGAAGTACGATGGTTAA

GCAGGCGAAAGAAATTGTGACATACATCCCTGAGCGGCTGCATAAAACG

TAG.
```

The mchB genes encodes the pre-microcin H47 peptide. Once the peptide product of the mchB gene has gone through modification and secretion steps, the pre-microcin H47 peptide becomes microcin H47.

mchB gene sequence:
```
                                    (SEQ ID NO: 4)
ATGCGAGAAATAACAGAATCACAGTTAAGATATATTTCCGGGGCG

GGAGGTGCGCCAGCGACTTCAGCTAATGCCGCAGGTGCTGCAGCTATTGT

TGGAGCTCTCGCCGGAATACCTGGTGGTCCACTTGGGGTTGTAGTTGGAG

CCGTATCTGCCGGTTTGACAACAGCAATTGGCTCGACCGTGGGAAGTGGT

AGTGCCAGTTCTTCTGCTGGTGGCGGTAGCTAA.
```

The mchE and mchF genes encode secretion proteins, which are necessary for secretion out of the cell. In some embodiments, the secretion proteins encoded by mchE and mchF are required for export of the microcin, but are not required for the production of the microcin.

mchE gene sequence:
```
                                    (SEQ ID NO: 5)
TTGTTTCGTCAGGATGCTTTAGAAAACAGAAAAATGAAGTGGCAGGGACG

GGCAATATTACTTCCCGGAATACCACTATGGTTAATCATGCTGGGAAGCA

TTGTGTTTATTACGGCATTTCTGATGTTCATTATTGTTGGTACCTATAGC

CGCCGTGTTAATGTCAGTGGTGAGGTCACAACCTGGCCAAGAGCTGTCAA

TATATATTCAGGTGTACAGGGATTTGTTGTCAGGCAATTTGTTCATGAA

GGGCAGTTGATAAAAAAAGGGGATCCTGTTTATCTGATTGACATCAGTAA

AAGTACACGTAGTGGTATTGTCACTGATAATCATCGGCGGGATATAGAAA

ATCAGCTGGTTCGTGTGGACAACATTATTTCCCGTCTGGAAGAAAGTAAA

AAAATAACGTTAGATACCCTGGAAAAACAACGTCTGCAATACACAGATGC

GTTTCGTCGCTCATCAGATATTATACAGCGTGCAGAGGAAGGGATAAAA

TAATGAAAACAATATGGAGAATTACAGAAACTATCAGGCAAAAGGGCT

GATTAATAAAGATCAGTTAACTAACCAGGTGGCATTATATTATCAGCAAC
```

-continued

AAAACAATCTTCTCAGCCTGAGCGGACAGAACGAACAGAATGCCCTGCAG

ATAACCACTCTGGAGAGTCAGATTCAGACTCAGGCTGCAGATTTTGATAA

CCGTATCTACCAGATGGAACTGCAACGGTACGAGTTACAGAAAGAACTGG

TTAACACTGATGTGGAGGGCGAAATTATTATCCGGGCGTTGACTGACGGG

AAAGTTGACTCCCTGAGTGTCACTGTCGGGCAAATGGTCAATACCGGAGA

CAGCCTTCTGCAGGTTATTCCTGAGAACATTGAAAACTATTATCTTATTC

TCTGGGTCCCAAATGATGCTGTTCCTTATATTTCGGCTGGTGACAAAGTG

AATATTCGTTATGAAGCCTTTCCGGCAGAAAAATTTGGGCAGTTCTCTGC

TACGGTTAAAACTATATCCAGGACTCCTGCGTCAACACAGGAAATGTTGA

CCTATAAGGGTGCACCACAGAATACGCCGGGCGCCTCTGTTCCCTGGTAT

AAAGTCATTGCGATGCCTGAAAAGCAGATTATCAGATATGACGAAAAATA

CCTCCCTCTGGAAAATGGAATGAAAGCCGAAAGTACACTATTTCTGGAAA

AAAGGCGTATTTACCAGTGGATGCTTTCTCCTTTCTATGACATGAAACAC

AGTGCAACAGGACCGCTCAATGACTAA.

mchF gene sequence:
(SEQ ID NO: 6)
ATGACTAACGGGAGTTTCAGACAAATTATAAATCAGCTTGATATGCGCTG

GCGACGTCGTGTTCCGGTTATTCATCAGACGGAGACCGCTGAATGTGGAC

TGGCCTGCCTGGCAATGATATGCGGTCATTTTGGTAAGAATATTGACCTG

ATATCTCTTCGCCGGAAGTTTAATCTCTCGGCCCGTGGAGCAAACCTTGC

AGGAATCAATGGAATAGCGGAGCAGCTGGGGATGGTCACCCGGGCTCTTT

CACTGGAGCTGGATGAACTTGGTGCCCTCAAAATGCCGTGTATTCTCCAC

TGGGATTTCAGTCACTTTGTCGTGCTGGTCAGCGTAAAGCGTAACCGTTA

TGTACTGCATGATCCGGCCAGAGGCAGAAGATATCTCGGTCGGGAGGAAA

TGAGCCGGTATTTTACGGGCATTGCACTTGAGGTCTGGCCTGGAAGTGAA

TTCCTGGCGGAAACCCAGCAGATCCGCATAAGTCTCCGTTCACTGATTAA

CAGTATTTACGGTATTAAAAGAACACTGGCGAAAATTTTCTGTCTGTCAG

TTGTAATTGAAGCAATCAATCTGGTAATGCCGGTGGGGACTCAGCTGGTT

ATGGATCATGCGATTCCGGCGGGGGACAGAGGGCTGCTGACGCTTATTTC

TGCTGGCCTGATGTTCTTTATATTGCTCAGGGCCGCGGTGAGTATGCTGC

GTGCATGGTCCTCACTGGTTATGAGCACGCTCATCAATATACAGTGGCAG

TCGGGTCTGTTTAACCATCTTCTCAGACTGCCGCTGGCGTTTTTTGAACG

CCGTAAATTAGGTGATATCCAGTCGCGTTTTGGCTCCCTTGACACTTTGA

GGGCCACCTTTACCACCTGTGTGGTTGGGGCAATCATGGACAGTATTATG

GTTGTGGGGGTTTTTGTGATGATGCTGTTATATGGAGGATATCTTACCTG

GATAGTGCTCGGTTTTACCATGGTTTACGTTCTTATTCGTCTGGTGACAT

ACGGCTATTACCGGCAAATATCGGAAGAAACTCTTGTCAGGGGGGCCCGG

GCCAGCTCCTATTTTATGGAAAGCCTGTATGGTATTGCCACGGTAAAAAT

CCAAGGTATGGCTGGGATCCGGGGAACACACTGGCTTAACCTGAAAATAG

ATGCGATCAATTCAGGTATTAAGTTAACCAAGATGGATTTGCTCTTCGGG

GGGATAAATACTTTTGTTGCCGCCTGTGATCAGGTGGCGATTTTATGGCT

-continued

GGGTGCAAGCCTTGTGATCGATAATCAGATGACAATAGGGATGTTTGTGG

CATTTGGTTCTTTTCGTGGGCAGTTTTCGGATCGGGTTGCTTCGCTGACC

AGTTTTCTTCTTCAACTGAGAATAATGAGTCTGCATAATGAGCGCATTGC

AGATATTGCACTACATGAAAAGGAAGAAAAGAAACCGGAAATTGAAATCG

TTGCTGACATGAGCCCGGTTTCACTGGAAACCACTGATTTAAGCTACCGG

TATGACAGCCAGTCAGCACAGGTATTCAGTGGTCTGAATTTGTCTGTGGC

TCCGGGAGAAAGTGTGGCTATAACTGGTGCCTCCGGTGCCGGAAAAACCA

CATTAATGAAAGTATTATGTGGACTGTTTGAACCAGATAGTGGAAAAGTA

CTGGTTAATGGCACGGATATACGTCAACTTGGAATAAATAATTATCACCG

TATGATAGCCTGTGTTATGCAGGACGACCGGCTATTTTCAGGATCAATTC

GTGAAAATATCTGTGGGTTTGCAGAAGAAACAGACGACGAATGGATGACA

GAATGTGCCAGAGCAAGTCATATTCATGATGTGATAATGAAAATGCCAAT

GGGGTATGAAACGTTAATAGGTGAACTGGGGGAAGGTCTTTCCGGCGGTC

AAAAACAGCGTATATTCATTGCCCGAGCTTTATACCGGAAACCTGGAATA

TTATTTATGGATGAGGCTACAAGTTCTCTTGATACAGAAAGTGAACGTTT

CGTGAATGCTGCCATAAAAAAATGAATATCACCCGGGTGATTATTGCAC

ACAGAGAAACTACGTTGAGAACTGTTGACAGGATTATTTCTATTTAA.

The mchI gene encodes for the MccH47 immunity protein.

mchI gene sequence:
(SEQ ID NO: 7)
ATGAGTTATAAAAAACTGTACCAATTGACGGCTATATTTAGTTTACCTCT

TACTATCTTATTGGTTTCACTTTCATCCCTTCGGATTGTTGGCGAAGGGA

ATTCTTATGTTGACGTTTTTCTAAGCTTTATAATATTTCTTGGTTTTATT

GAGCTGATTCATGGGATTCGAAAGATTTTGGTCTGGTCAGGCTGGAAAAA

CGGAAGTTAA.

mchX gene sequence:
(SEQ ID NO: 8)
ATGGAATTTGCTACAAACAGGGTTACTGTAAATGACAGTCGGTCAGCACT

GTCATCAACTTTGCTGTTGTCTTTGATCATGAGCGCCACTCTACTGGAAT

ATTCTTATCGATGACCTGA.

mchS1 gene sequence:
(SEQ ID NO: 9)
ATGAAAAACTATCTTTTCCAGACTCCCGAAGATATTTGTGTACAGTTAAA

AAAAATGACACATCCTGTCACAATAAGAACAACAGATATTGCTAATTTCT

GGCACTATCTTGAGTCAGCAACTCTTCCGGTGATCACAAAAAGCACCACT

ACAGAAAATCGGGAGGTTACATTTCTGTGGCGCTCAGAGAAAGCAGTGCA

AGGCGTATATCTTCGCCTGAATCGTGTTACAGATAAAAAAGATGTCAAAA

AAGGACTAATGACTCATATCCCTTCGACAGATATCTGGATGCTGACACTG

GTGTTACCAGCTTCATATCGGGGCTCATACTCATTTATAGAAATTCCCAC

AGATATGACACAAAAGACATATTTCAACTAGGAAGTCGCTTCTCTCCAT

TACCCGGTAAATCTGATCCATTTAACAAAACAGCAGAAATAAATATACGA

GGATTCGGAGAATCAGTCCTTTCTCTTGATATGGCTCCTGAACAAAAGGA

-continued

ATGGGATGATACTTCCCATAAATGTACAGGTATTCTTTCAACATTACATT

CCTTTGTTGCAGGATATCAACGCCGGATTCGTTTATATTTTCCCCAGAAT

CCAACATCAGTACCTCTTGGATTACTTGTGTTACCTGATGCTGAAATATG

GTTTGACCGGATGGATATTACCCGGGCATTAGATATGGCCATTACCACTG

GTCATATTGCGCCAATGGCAATTATGGGGATAGACAATATTAATGAATCT

GATCGTATGAATATACTGGGAGGCAATAAAGAACTTATCTTTGATATAGC

GGAAAATCTGATACCCCAGTTATACAGAGACTACCCGAATATCGTATGGG

CTGGTCGTTCTAATACTATACTGGCCGGTCAGAGCCTCGGTGGAGTGACA

GCACTGATGGCAGCTATATATGCGTCGACAACATTTGGTACAATCATTAG

CCACTCACCTTCAATGTGGTGGAACCCTGACCAGGGCAGCCCGATTTTGT

TTACTGAGAATGATATCTCCTGGGTAAGTGAGCAGATACTTTCAGCGCCT

CCGAAAGATGTAAATATCCAACTTGGAGTCGGTTCTTTAGAAGGTACAAC

CGTCTCACATGTTCAGCGGTTGCATCAGTCGTTAATCGCAGCAGGTTTGG

AAAGTAACCTCACTGTCTATGCCGGTGGTCATGATTATGCCTGGTGGCGC

GGAGCAATTATTGATGCATTAGCAAATTATAATTGCAGGAAGATATCAGA

TAATAACTTTGTGTAA.

mchS4 gene sequence:
(SEQ ID NO: 10)
ATGAATTGTGATAATAATCACAGAAATGAAGAATTCATTGTTACCTTTGA

TAAAGGCAACAAGCAAGACAATTCAAGACGAAAACACGATAATTTTCCTA

TAGAGGTAGAATCCTCCGTAGAGCTGGAGACACACTGTATCACAAATAAT

AAGTCGGCTTCCGGTATAGTAACACATGACTATGATGCCGATTATATTTG

TGGTTGTGGTGAAATTATGTGTCCTGGTTGCGGTCATGACCTATAA.

The mciA (formerly known as mchS2) gene encodes the pre-microcin I47 peptide. Once the peptide product of the mciA gene has gone through modification and secretion steps, the pre-microcin I47 peptide becomes microcin I47.

(SEQ ID NO: 11)
ATGAGAGAAATATCAGATAACATGCTTGATTCCGTGAAAGGAGGGAT

GAATCTTAATGGATTACCTGCTTCTACTAATGTAATAGATCTACGTGGA

AAAGATATGGGAACATATATTGATGCTAATGGAGCATGCTGGGCTCCGGA

TACTCCATCCATCATCATGTATCCGGGGGGAAGTGGACCTTCTTATAGTA

TGAGTAGTTCCACATCCAGTGCAAACAGCGGCAGTTAA

The mciI (formerly known as mchS3) gene encodes for the MccI47 immunity protein.

mciI gene sequence:
(SEQ ID NO: 12)
ATGTATCTTACGAAAAAGATTATAATAAGTATGATGTTTATATTACCATC

TGCTGCATTTTCATCAGATCCACCTCCCCTTCAACAATCGTTAGAAAAAA

CAACCTATTTTTCTATAGGTATGAATGGGTTTATAGGCTATCAGAGCGAA

GGGGAAAAATTATACACACACATTCTTACATTAGATAATCCCGAAGAGAT

ATTTAAAAATATAATAAAAAATAGAAAGTCAACTAAGGAGTCTAAAATTT

ATGCTGCTTGTGGGCTATATTATTTAAACGTAGAAAATATAGAGTCATTG

-continued

TTTAATGAAAATGATAAACAAGAATATGTGTCTGTCTTAAGAGGGGATAT

TTTAACAAAAATAAAACTGAATGATATTCTGAATTCTGTGATAATAAATG

GTTGCAACACCAAATTAATATCTGAACATAAATGA.

Vectors

This disclosure provides various vectors comprising microcin genes and controllable promoters (e.g., inducible promoters). In some embodiments, the vector is a plasmid (e.g., pBBAD, pS4BAD, pJBAD, pBR322, pLJV3, and pEX2000).

The vector can include genes for various microcins, e.g., Class I microcins, Class IIa microcins, Class IIb microcins, and/or Class IIc microcins. In some embodiments, the vector can include a set of genes for a Class IIa microcin (e.g., MccH47, MccE492, MccM, MccG492, and MccI47). In some embodiments, the vector can include a set of genes for MccI47.

In some embodiments, the vector includes a set of genes for MccI47. These genes are required to express a functional MccI47 that can inhibit the growth of other bacteria. In some embodiments, the set of genes includes one, two, three, four, five, six, seven, or eight genes that are selected from the group consisting of mchA, mchB, mchC, mchD, mchE, mchF, mchX, mchI, mchS1, mchS4, mciI and mciA. In some embodiments, the set of genes includes mchA, mchC, and mchD. In some embodiments, the set of genes includes mchA, mchC, mchD, mchE, and mchF (pBBAD). In some embodiments, the set of genes includes mchA, mchC, mchD, mchE, mchF, and mchS4 (pS4BAD). In some embodiments, the set of genes includes mchA, mchC, mchD, mchE, mchF, mchS1, and mchS4 (pJBAD).

In some embodiments, the set of genes includes mchA, mchC, mchD, mchE, mchF, mciI, and mciA (pBBAD-I47). In some embodiments, the set of genes includes mchA, mchC, mchD, mchE, mchF, mchS4, mciI, and mciA (pS4BAD-I47). In some embodiments, the set of genes includes mchA, mchC, mchD, mchE, mchF, mchS1, mchS4, mciI, and mciA (pJBAD-I47). In some embodiments, the minimum genes required for the production of active, mature microcin I47 are mciIA and mchACD. In some embodiments, the set of genes includes mchA, mchC, mchD, mciI and mciA.

In some embodiments, the vector for the production of active, mature microcin I47 is constructed by combining a plasmid expressing mciI and mciA, a plasmid expressing mchC, mchD, mchE, and mchF, and a plasmid expressing mchA. In some embodiments, the vector for the production of active, mature microcin I47 is constructed by combining a plasmid expressing mciI and mciA, a plasmid expressing mchC, mchD, mchE, and mchF, and a plasmid expressing mchA, and mchS4. In some embodiments, the vector for the production of active, mature microcin I47 is constructed by combining a plasmid expressing mciI and mciA, a plasmid expressing mchC, mchD, mchE, and mchF, and a plasmid expressing mchA, mchS1 and mchS4. In some embodiments, the plasmids are combined into a single backbone vector, e.g., pUC19.

In some embodiments, the vector includes a set of genes for MccH47. These genes are required to express a functional MccH47 that can inhibit the growth of other bacteria. In some embodiments, the set of genes includes mchA, mchB, mchC, mchD, mchI, ad mchX. In some embodiments, the set of genes includes mchA, mchB, mchC, mchD, mchE, mchF, mchI, and mchX (pBBAD-H47). In some embodiments, the set of genes includes mchA, mchB, mchC, mchD, mchE, mchF, mchI, mchS4, and mchX (pS4BAD-H47). In some embodiments, the set of genes includes mchA, mchB, mchC, mchD, mchE, mchF, mchI, mchS1, mchS4, and mchX (pJBAD-H47). In some embodiments, the minimum genes required for the production of active, mature microcin H47 are mchXIB and mchACD. In some embodiments, the set of genes includes mchA, mchB, mchC, mchD, mchI, ad mchX.

In some embodiments, one or more genes in a set of genes are located within one operon. In some embodiments, the set of genes are located within more than one operons. Thus, in some embodiments, the operon includes one, two, three, four, five, six, seven, eight, or nine, or ten genes.

In some embodiments, the vector for the production of active, mature microcin H47 is constructed by combining a plasmid expressing mchX, mchI and mchB, a plasmid expressing mchC, mchD, mchE, and mchF, and a plasmid expressing mchA. In some embodiments, the vector for the production of active, mature microcin H47 is constructed by combining a plasmid expressing mchX, mchI and mchB, a plasmid expressing mchC, mchD, mchE, and mchF, and a plasmid expressing mchA, and mchS4. In some embodiments, the vector for the production of active, mature microcin H47 is constructed by combining a plasmid expressing mchX, mchI and mchB, a plasmid expressing mchC, mchD, mchE, and mchF, and a plasmid expressing mchA, mchS1 and mchS4. In some embodiments, the plasmids are combined into a single backbone vector, e.g., pUC19.

In some embodiments, the set of genes or the operon is under the control of a controllable promoter. As used herein, the term "controllable promoter" refers to a promoter of which the initiation of transcription is controllable. For example, the initiation of transcription of a controllable promoter can be induced by a ligand, such as tetracycline, arabinose, galactose, isopropyl β-D-1-thiogalactopyrano-side (IPTG), allolactose, etc. In some embodiments, the controllable promoter is rhaPBAD or Pttr.

High levels of microcins may be harmful to a subject, thus, according to the present disclosure, mechanisms can be introduced to the genetically engineered microorganisms to control the transcription of the genes or the operon, and thus control the level of microcins. The transcription of the microcin genes can be controlled by a controllable promoter. Some exemplary controllable promoters include, but are not limited to, Pttr promoter or pBAD promoter. The pBAD promoter is found in bacteria and was originally part of the arabinose operon that regulates transcription of araB, araA, and araD. Transcription initiation at the pBAD promoter occurs in the presence of high arabinose and low glucose concentrations. Upon arabinose binding to AraC, the N-terminal arm of AraC is released from its DNA binding domain via a "light switch" mechanism. This allows AraC to dimerize and bind the I1 and I2 operators. The AraC-arabinose dimer at this site contributes to activation of the pBAD promoter. Additionally, cyclic AMP receptor protein (CAP) binds to two CAP binding sites upstream of the I1 and I2 operators and helps activate the pBAD promoter. In the presence of both high arabinose and high glucose concentrations however, low cAMP levels prevent CAP from activating the pBAD promoter. In the absence of arabinose, AraC dimerizes while bound to the O2 and I1 operator sites, looping the DNA. The looping prevents binding of CAP and RNA polymerase. Thus, without arabinose, the pBAD promoters are repressed by AraC. A detailed description of pBAD promoter can be found, e.g., in Schleif R. AraC protein, regulation of the L-arabinose operon in *Escherichia*

*coli*, and the light switch mechanism of AraC action. FEMS Microbiol. Rev., (2010) 1-18, which is incorporated by reference in its entirety.

pBAD promoter sequence:
(SEQ ID NO: 13)
CCACAATTCAGCAAATTGTGAACATCATCACGTT-
CATCTTTCCCTGGTTGCC

AATGGCCCATTTTCCTGTCAGTAACGAGAAGGTCGCGTATTCAGGCGCTTT

TTAGACTGGTCGTAATGAA.

In some embodiments, the controllable promoter is Pttr and is activated in the presence of tetrathionate as the inducing agent. The vector can also include genes that are required to determine the level of tetrathionate. Thus, the vector can include one, two, three, four or five genes that are selected from the group consisting of ttrA, ttrB, ttrC, ttrS, and ttrR. In some embodiments, the vector includes ttrS and ttrR.

In some embodiments, ttrA, ttrC, and ttrB are located within one operon. In some embodiments, this operon further includes mchB, mchC, mchD, mchE, mchF, mchX and mchI. In some embodiments, this operon is under the control of Pttr.

In some embodiments, the tetrathionate promoter (Pttr) is located immediately upstream of the mchXIB genes (mchX, mchI, mchB), and encoding them on a single transcript based on activation of the ttr promoter. The mchA can controlled by a constitutive promoter (e.g., J23119).

Pttr promoter sequence:
(SEQ ID NO: 14)
CCCAATATCCCTGTCAATTATGTTGTTTTAGAT-
CAACAACAAGCCGGGTATG

TGGTTAACCACAATAGAGCGCACCCCGCCTCGATTTTTACACTGTAAAT-
CAT

CGACATTTTTTATTCATTACACATGAACCAACATCGTGACAAATGTTT-
CATT

GTTGGCA.

J23119 promoter sequence:
(SEQ ID NO: 15)
TTGACAGCTAGCTCAGTCCTAGGTATAATGCTAG.

This disclosure further provides genetically engineered microorganisms comprising the vectors as described herein. In some embodiments, the vector are integrated into the genome of the microorganism, e.g., by recombinant DNA techniques. Thus, in one aspect, this disclosure provides an engineered strain of EcN harboring a plasmid-based system carrying mchACDEF, mciI, mciA, and ttr RSBCA, capable of producing MccI47 in response to environmental tetrathionate, resulting in the ability to inhibit and out-compete *Salmonella*. In another aspect, this disclosure provides an engineered strain of EcN harboring a plasmid-based system carrying mchAXIBCDEF, and ttrRSBCA, capable of producing MccH47 in response to environmental tetrathionate, resulting in the ability to inhibit and out-compete *Salmonella*.

Genetically Engineered Microorganisms

Many microorganisms can be genetically engineered to treat bacterial infection as described herein. In some embodiments, a bacterium is used. In some embodiments, the bacterium is *E. coli* (e.g., *E. coli* Nissle 1917 or *E. coli* NGF-19). One useful *E. coli* strain is Nissle 1917 (EcN). *E. coli* Nissle 1917 is a Gram-negative species, which is easily cultured, easily genetically manipulated, able to colonize a human host, and easy to use for human probiotic applications. EcN is the active component of Mutaflor® (Ardeypharm GmbH, Herdecke, Germany), a microbial probiotic drug that is marketed and used in several countries. Clinical trials have shown EcN to be effective for maintaining remission of ulcerative colitis (UC), for stimulation of the of the immune system in premature infants, for treatment of infectious GI diseases, for the relief of constipation, and also for treatment of Irritable Bowel Syndrome in some patients.

In some embodiments, useful microorganisms that can be used in the methods disclosed herein include bacteria for making yogurt, e.g., *Lactobacillus delbrueckii* subsp. *bulgaricus* and *Streptococcus thermophiles*.

A vector or a set of genes as described herein can be introduced into a microorganism, e.g., a bacterium, such as, *E. coli*, to generate a genetically engineered microorganism by known molecular biology, microbiology, and recombinant DNA techniques. These techniques are familiar to one of skilled in the art and are explained fully in the literature. See, e.g., Molecular Cloning: A Laboratory Manual (Michael R. Green, Joseph Sambrook, Fourth Edition, 2012); Oligonucleotide Synthesis: Methods and Applications (Methods in Molecular Biology) (Piet Herdewijn, 2004); Nucleic Acid Hybridization (M. L. M. Andersen, 1999); Short Protocols in Molecular Biology (Ausubel et al., 1990), each of which is incorporated herein by reference in its entirety.

In some embodiments, the vector or the set of genes is integrated into the bacterial or other microbial genome.

Examples of bacterial species that can be used as engineered microorganisms include, but are not limited to: *Acinetobacter baumannii, Enterobacter cloacae, Escherichia coli, Klebsiella oxytoca, Klebsiella pneumonia, Proteus mirabilis, Pseudomonas aeruginosa, Salmonella typhimurium, Salmonella typhi, Serratia marcescens, Shigella flexneri*, and *Staphylococcus aureus.*

Methods of Treating Bacterial Infection

Mcc147 has been shown to be active to inhibit various bacteria, e.g., gram-negative bacteria. As used herein, the term "gram-negative bacterium" refers to a bacterium that do not retain the crystal violet stain used in the Gram staining method of bacterial differentiation. Gram-negative bacteria include, e.g., proteobacteria, cocci, bacilli, etc. The proteobacteria are a major group of gram-negative bacteria, including *Escherichia coli (E. coli), Salmonella, Shigella*, and other Enterobacteriaceae, *Pseudomonas, Moraxella, Helicobacter, Stenotrophomonas, Bdellovibrio*, acetic acid bacteria, *Legionella* etc. Gram-negative bacteria also include, e.g., the cyanobacteria, spirochaetes, green sulfur, and green non-sulfur bacteria. Medically relevant gram-negative cocci include, e.g., *Neisseria gonorrhoeae, Neisseria meningitidis*, and *Moraxella catarrhalis, Haemophilus influenzae*. Medically relevant gram-negative bacilli include a multitude of species. Some of them cause primarily respiratory problems (*Klebsiella pneumoniae, Legionella pneumophila, Pseudomonas aeruginosa*), primarily urinary problems (*Escherichia coli, Proteus mirabilis, Enterobacter cloacae, Serratia marcescens*), and primarily gastrointestinal problems (*Helicobacter pylori, Salmonella enteritidis, Salmonella typhi*). Gram-negative bacteria associated with hospital-acquired infections include, e.g., *Acinetobacter baumannii*, which cause bacteremia, secondary meningitis, and ventilator-associated pneumonia in hospital intensive-care units.

In some embodiments, the composition and the methods as described herein can be used to treat gram-negative bacterial infection. In some embodiments, the bacterial infection is carbapenem-resistant Enterobacteriaceae infection, *Klebsiella oxytoca* infection, *Klebsiella pneumoniae* infection, *Campylobacter* infection, extended spectrum Enterobacteriaceae (e.g., *E. coli, Salmonella, Shigella* and *Yersinia*) infection.

The methods described in the present disclosure are effective for treating bacterial infection in a variety of subjects including humans and animals, such as laboratory animals, e.g., mice, rats, rabbits, or monkeys, or domesticated and farm animals, e.g., cats, dogs, goats, sheep, pigs, cows, horses, and birds, e.g., chickens and turkeys.

Healthcare providers can identify subjects in need of treatment for bacterial infection using their experience and judgment, which can be based on subjective (e.g., based on the healthcare provider's opinion) or objective (e.g., measurable by a test or diagnostic method) information. As used herein, the terms "treat," treating," "treatment," and the like refer to reducing or ameliorating a disorder and/or symptoms associated therewith. It will be appreciated that, although not precluded, treating a disorder or condition does not require that the disorder, condition, or symptoms associated therewith be completely eliminated.

The present disclosure provides methods of inhibiting or reducing the risk of bacterial infections and for treating bacterial infections. As used herein, the term "reducing the risk" refers to reducing the probability of developing a disorder or condition in a subject, who does not have, but is at risk of, or susceptible to, developing a disorder or condition.

In some embodiments, the genetically engineered microorganisms can be administered to a subject with some other known treatments for bacterial infection. For example, the genetically engineered microorganisms can be used in combination with an antibiotic therapy, such as metronidazole, vancomycin, bacitracin, and/or teicoplatin. In some embodiments, the genetically engineered microorganisms are administered to the subject after the subject have received an antibiotic therapy. In some embodiments, the genetically engineered microorganisms are administered to the subject before the subject has received an antibiotic therapy. In other embodiments, the genetically engineered microorganisms are administered to the subject when the subject is under an antibiotic therapy.

In some embodiments, the genetically engineered microorganisms can be administered to a subject with alkaline phosphatase. These methods involve administering to the subject a composition including the genetically engineered microorganisms and an amount of an alkaline phosphatase effective to increase the number of commensal bacteria in the gastrointestinal tract, wherein alkaline phosphatase decreases the number of pathogenic bacteria in the gastrointestinal tract, or increases the number of commensal bacteria and decreases the number of pathogenic bacteria in the gastrointestinal tract, thereby modulating gastrointestinal tract flora levels in the subject. The alkaline phosphatase composition, and the methods of use is described in WO 2010/025267, which is incorporated by reference in its entirety.

Methods of Treating Dysbiosis

The compositions and the methods as described herein can be used to treat and/or reduce the risk of dysbiosis and its associated diseases.

Dysbiosis is a term for a microbial imbalance or maladaptation on or inside the body. As used herein, the term "intestinal dysbiosis" refers to microbial imbalance in intestines. Dysbiosis is most commonly reported as a condition in the gastrointestinal tract, particularly during small intestinal bacterial overgrowth (SIBO) or small intestinal fungal overgrowth (SIFO). It has been reported to be associated with various diseases, such as periodontal disease, inflammatory bowel disease, chronic fatigue syndrome, obesity, cancer, bacterial vaginosis, and colitis.

The methods described in the present disclosure are effective for treating dysbiosis in a variety of subjects including humans and animals, such as laboratory animals, e.g., mice, rats, rabbits, or monkeys, or domesticated and farm animals, e.g., cats, dogs, goats, sheep, pigs, cows, horses, and birds, e.g., chickens and turkeys.

Healthcare providers can identify subjects in need of treatment for dysbiosis using their experience and judgment, which can be based on subjective (e.g., based on the healthcare provider's opinion) or objective (e.g., measurable by a test or diagnostic method) information. As used herein, the terms "treat," treating," "treatment," and the like refer to reducing or ameliorating a disorder and/or symptoms associated therewith. It will be appreciated that, although not precluded, treating a disorder or condition does not require that the disorder, condition, or symptoms associated therewith be completely eliminated.

The present disclosure provides methods of inhibiting or reducing the risk of dysbiosis and for treating dysbiosis. As used herein, the term "reducing the risk" refers to reducing the probability of developing a disorder or condition in a subject, who does not have, but is at risk of, or susceptible to, developing a disorder or condition.

In some embodiments, the genetically engineered microorganisms can be administered to a subject with some other known treatments for dysbiosis.

Methods of Administration

The therapeutic methods disclosed herein (including prophylactic treatments) generally include administration of a therapeutically effective amount of a composition comprising the genetically engineered microorganisms to a subject in need thereof. Such treatment will be suitably administered to subjects, particularly humans, suffering from, having, susceptible to, or at risk for a disease, disorder, or symptom of bacterial infection and/or dysbiosis. Determination of those subjects who are "at risk" can be made by any objective or subjective determination by a diagnostic test or opinion of a health care provider.

A subject is effectively treated when a clinically beneficial result ensues. This may mean, for example, a resolution of the symptoms associated with bacterial infection and/or dysbiosis, a decrease in the severity of the symptoms associated with bacterial infection and/or dysbiosis, or a slowing of the progression of symptoms associated with bacterial infection and/or dysbiosis.

The compositions can also include a pharmaceutically acceptable carrier. The term "pharmaceutically acceptable" refers to molecular entities and compositions that do not produce an adverse, allergic or other untoward reaction when administered to a subject. The term "pharmaceutically acceptable carrier," as used herein, includes any and all solvents, dispersion media, coatings, antibacterial, isotonic and absorption delaying agents, buffers, excipients, binders, lubricants, gels, surfactants and the like, that may be used as media for a pharmaceutically acceptable substance.

Compositions comprising the genetically engineered microorganisms can be administered to a subject through many different routes, e.g., by endoscopy, by enteroscopy, by colonoscopy, by a nasoduodenal catheter, by enema, or by oral administration. In the case of oral administration, the composition can be delivered in a capsule or pill form, e.g., for intestinal delivery. In some embodiments, the composition is in a capsule form, e.g., packaged in gelatin capsules.

The present disclosure also provides a food composition comprising the genetically engineered microorganisms. In some embodiments, the food composition comprises carbohydrates such as, but not limited to, starches such as are contained in rice flour, flour, tapioca flour, tapioca starch, and whole wheat flour, modified starches or mixtures thereof.

In some embodiments, the compositions including the genetically engineered microorganisms are in the form of a liquid, and thus can be used as a beverage. In some embodiments, the beverage composition comprising the genetically engineered microorganisms is naturally sweetened. Suitable natural sweeteners include, but are not limited to, sugars and sugar sources such as sucrose, lactose, glucose, fructose, maltose, galactose, corn syrup (including high fructose corn syrup), sugar alcohols, maltodextrins, high maltose corn syrup, starch, glycerin, brown sugar and mixtures thereof.

In some embodiments, the food or beverage compositions include milk or milk-derived product, e.g., yogurt. In some embodiments, a stabilizer may be combined with the milk-derived product. Combining a stabilizer with the milk-derived product may thicken the milk-derived product. In some embodiments, a stabilizer can be combined with the milk-derived product following completion of microorganism culture. The stabilizer can be selected from, as examples, gums, salts, emulsifiers, and their mixtures. Gums can be selected from, as examples, locust bean gum, xanthan gum, guar gum, gum arabic, and carageenan. In some embodiments, salts include, but are not limited to, sodium chloride and potassium chloride.

Dosage

The compositions can be formulated in a unit dosage form, each dosage containing, for example, from about 0.005 mg to about 2000 mg of the genetically engineered microorganisms. The dosage scheduling can be approximately once per week, twice per week, three times per week, or four times per week. In some embodiments, the compositions can be administered to a subject every day, every other day, every three days, every four days, every five days, every six days, or once per week. A person skilled in the art can refine the dosage scheduling as needed.

The phrase "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. When referring to these pre-formulation compositions as homogeneous, the active ingredient is typically dispersed evenly throughout the composition so that the composition can be readily subdivided into equally effective unit dosage forms.

The compositions can be formulated in a unit dosage form, each dosage containing, for example, from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the genetically engineered microorganisms.

Kits

The present disclosure also provides kits of the genetically engineered microorganisms. In some embodiments, the kit includes a sterile container which contains a therapeutic or prophylactic composition having the genetically engineered microorganisms. Such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

The kit can also include instructions, e.g., information about the use of the composition for treating a bacterial infection. The kit can further contain precautions; warnings; indications; counter-indications; overdose information; adverse reactions; animal pharmacology; clinical studies; and/or references. The instructions may be printed directly on the container (when present), or as a label applied to the container, or as a separate sheet, pamphlet, card, or folder supplied in or with the container.

EXAMPLES

The invention is further described in the following examples, which do not limit the scope of the invention described in the claims.

Example 1: Construction and Analysis of Plasmid-Based Systems for the Production of Microcin H47 or Microcin I47

As outlined in the introduction, the mch gene cluster of *E. coli* strain H47 contains twelve genes: mchABCDEFIXS-1S4 and mciAI. Known or proposed functions were provided for all twelve. Notably, other *E. coli* strains containing parts, or all, of the mch cluster also occasionally contain three additional genes, mcmAIM. Strains of *E. coli* housing all twelve mch cluster genes, in addition to the mcmAIM genes include strains *E. coli* strain CA46 and *E. coli* strain CA58. Interestingly, *E. coli* strain Nissle (EcN) and a uropathogenic strain *E. coli* CFT073 lack mchS1S2S3, but have mcmAIM, while *E. coli* H47 has truncated versions of mcmAIM. As mentioned, mciAI were previously referred to as mchS2S3 and have been renamed, comprising the gene pair responsible for microcin I47 (MccI47) production and immunity. mcmAI are the corresponding gene pair encoding the peptide and immunity protein for microcin M (MccM), the third and final known member of the *E. coli*-derived Class IIb microcins. An overview of the known mch gene clusters is represented in FIG. 1.

The focus of the current study is two-fold. First, MccI47 inhibitory action against select Enterobacteriaceae representatives was determined. Second, inhibitory activity from three distinct vector backbones were compared to best determine best candidate mch genes to design vectors for eradication of enteric targets during an in vivo challenge study, specifically focused on the relevancy of mchS1 and mchS4.

The roles of MchS4 and MchS1 are known to be optional in the originally characterized host strain *E. coli* H47, but their functions could possibly affect inhibitory activity in terms of both potency and spectrum. First, MchS4 has no known homologs, with the Basic Local Alignment Search Tool (BLAST) returning results of >50% amino acid identity from other hypothetical proteins (seven, in total) exclusively from *E. coli*. However, in *E. coli* strain K-12, the presence of mchS4 led to elevated iron-chelating activity, allowing for enterobactin production even in iron-rich environments, while *E. coli* K-12 strains without mchS4 lack this capability[22]. This result demonstrates that MchS4 likely plays some role in enterobactin biosynthetic pathway regulation, as the two main pathways leading to enterobactin biosynthesis in *E. coli* are multi-enzymatic (shikimate and non-ribosomal peptide synthesis (NRPS)). Maturation of class IIb microcins is dependent upon linkage to catecholate siderophores, and therefore it is reasonable to presume that inclusion of mchS4 could lead to elevated levels of inhibitory activity by MccH47 and MccI47.

Unlike MchS4, MchS1 has numerous known homologs, all belonging to the Fes superfamily of enterochelin esterases (e.g. IroD, Fes), present in *E. coli* as well as other known siderophore producers (e.g. *Klebsiella, Salmonella, Serratia*). While enzymatic kinetics of MchS1 have not been specifically elucidated, Fes homologs have been purified to homogeneity and demonstrated to hydrolyze both enterobactin and the enterobactin ferric complex in vitro, though the former was more effectively hydrolyzed. Fes/MchS1 activity is represented in FIGS. 3A-3H. Interestingly, comparative studies of Fes, IroD, and IroE demonstrated that both IroD and IroE hydrolyze ferric enterobactin more effectively than their non-ferric counterparts, potentially justifying the presence of both Fes and IroD/IroE. It is unknown whether MchS1 hydrolyzes the ferric or non-ferric enterobactin more efficiently, though it has been demonstrated that expression of MchS1 in *E. coli* K-12 led to reduced iron chelating activity, implying degradation of non-ferric enterobactin prior to secretion taking place. Previous studies have purified MccM and MccE492 containing the mixture of a structural microcin peptide linked to $DHBS_3$, $DHBS_2$, and $DHBS_1$ and tested their inhibitory activity, but individual compounds of the mixture have not been tested and directly compared, to date. This collectively leads to the hypothesis that the presence of MchS1 may lead to altered inhibitory effect against variable targets, due to an alteration of $DHBS_3$:$DHBS_2$:$DHBS_1$.

Figure 2:
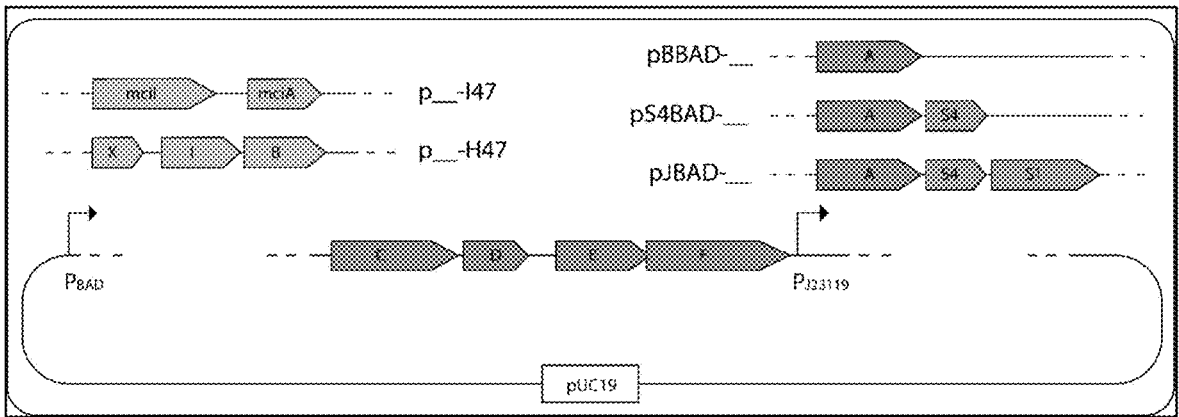
FIG. 2 is a diagram depicting the design of the six vectors used for MccH47 and MccI47 production. The first variable region inducibly expresses mchXIB or mciIA, and the second variable region express either mchA, mchAS4, or mchAS4S1. mchCDEFA are essential genes for MccH47 and MccI47 production and post-translational modification, while mchS4S1 are non-essential. mchCDEF retain their natural expression regulatory features, while mchXIB and mciIA are regulated by $P_{BAD}$ and mchAS4S1 are expressed from the strong constitutive promoter, $P_{J23119}$. All vectors are built into the high-copy pUC19, ColE1 origin backbone.
Figures 3A, 3B, 3C, 3D, 3E, 3F, 3G, 3H:
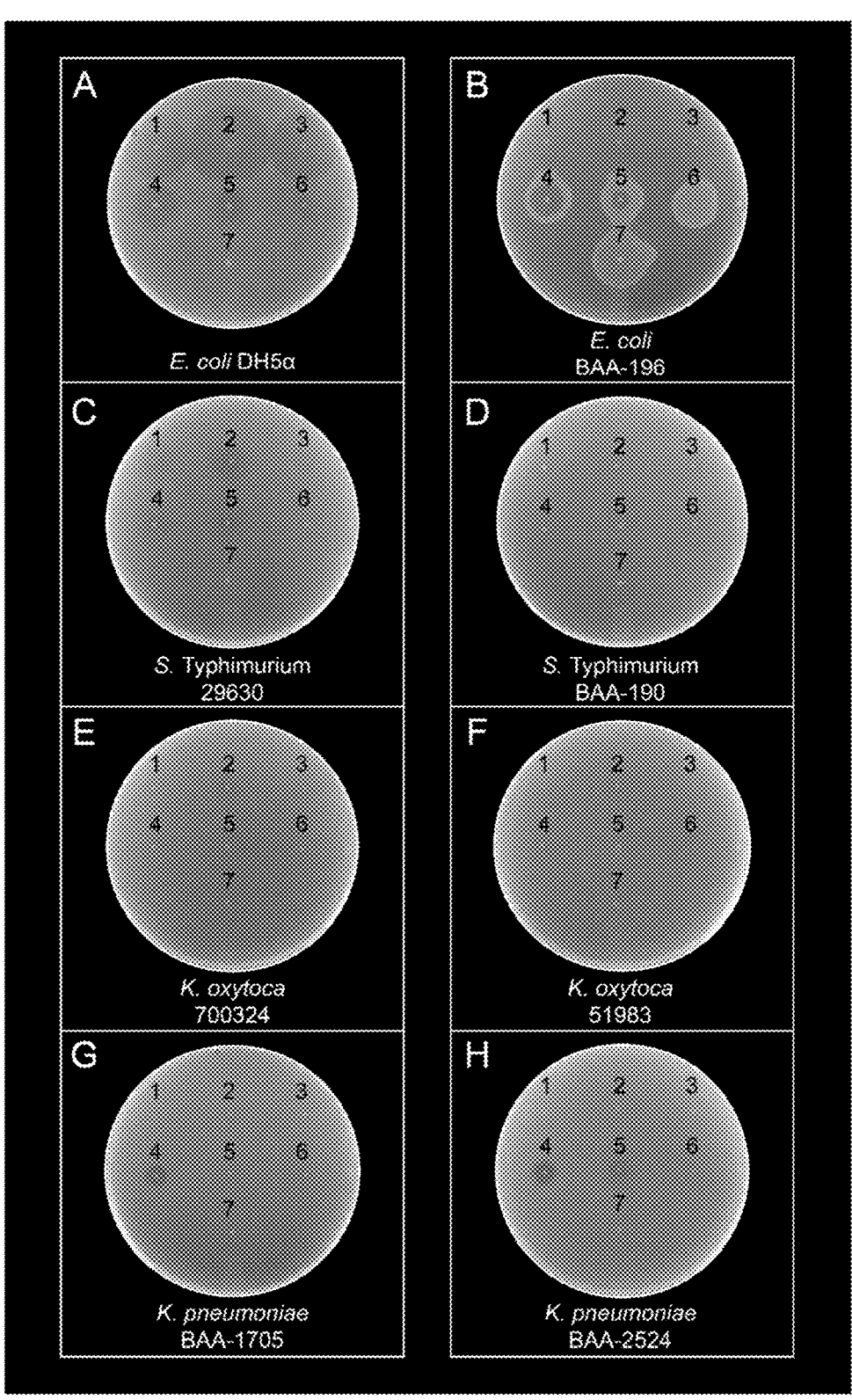
FIGS. 3A-3H are representations of assay plates showing results of static inhibitory assays utilizing stabs of *E. coli* NEB10β transformed with 1) pBBAD-H47, 2) pS4BAD-H47, 3) pJBAD-H47, 4) pBBAD-I47, 5) pS4BAD-I47, 6) pJBAD-I47, and 7) pUC19. Target overlays include A.) *E. coli* DH5α, B.) *E. coli* BAA-196, C.) *S. typhimurium* 29630 pUC19, D.) *S. typhimurium* BAA-190 E.) *K. oxytoca* 700324 pUC19, F.) *K. oxytoca* 51983, G.) *K. pneumoniae* BAA-1705, H.) *K. pneumoniae* BAA-2524. Target strains B, D, F, G, and H are classified as multidrug resistant.
Figures 4A, 4B, 4C, 4D:
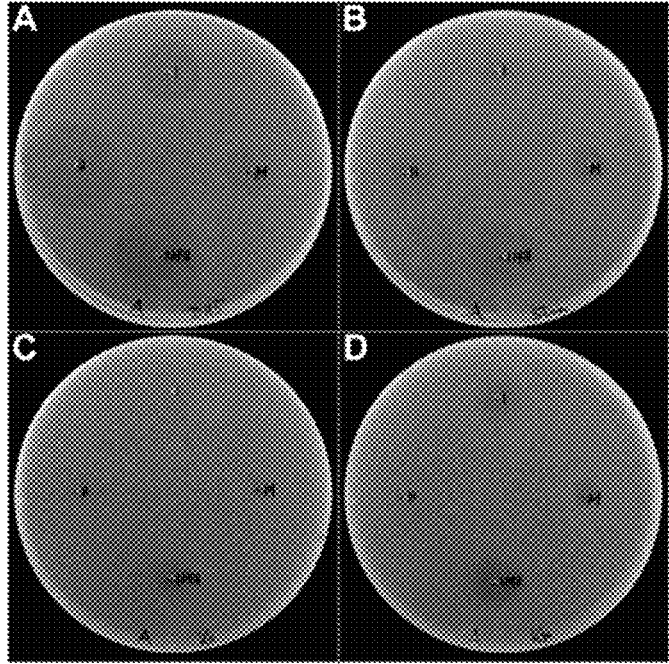
FIGS. 4A-4D are representations of assay plates showing results of static inhibitory assays utilizing stabs of *E. coli* NEB10β transformed with pBBAD-I47 against (A) *E. coli* DH5alpha, (B) *S. typhimurium*, (C) *K. oxytoca* and (D) Carbapenem-resistant *K. pneumoniae*. (Right) Plasmid overexpressing genes for I47 production and for its post-translational modification and export.

Siderophore scavenging Enterobacteriaceae often contain multiple siderophore receptors, which have been shown to have variable binding and transport efficiencies for different siderophores, and knockout mutants have variable susceptibility to different class IIb microcins. This phenomenon of apparent redundancy increases fitness in *P. aeruginosa*, allowing strains to switch between highly efficient, but metabolically costly siderophores and less efficient, less metabolically expensive siderophores. Considering this, altering investment of catecholate siderophores in a microcin producing strain towards $DHBS_3$ or $DHBS_1$ may have variable effect against any targets that tend to preferentially uptake more costly or less costly siderophores. Careful separation of compounds using advanced chromatography techniques may be the best method for testing this hypothesis, however, as a simple test of principle for this study, it will be assumed that strains with MchS1 (FIG. 2) likely produce a MccH47/MccI47 mixture more strongly skewed towards $MchB-DHBS_1$/$MciA-DHBS_1$, as compared with strains that lack MchS1 (FIG. 2).

Materials and Methods

The following materials and methods were used in the following examples.

Microbial Strains, Media, and Growth Conditions

Strains used in this study include *Escherichia coli* strain NEB10β (New England Biolabs. Ipswich, MA) and the strains listed utilized in FIGS. 3A-3H, all of which were purchased from ATCC, except for *E. coli* DH5α (New England Biolabs. Ipswich, MA). Plasmid constructs developed in this work were transformed by electroporation into *E. coli* NEB10β cells. All media and additional reagents listed in this study were purchased from Sigma Aldrich, St. Louis, MO, unless otherwise indicated.

Vectors pBBAD-H47, pS4BAD-H47, pJBAD-H47, pBBAD-I47, pS4BAD-I47, pJBAD-I47 were constructed using standard methods for Gibson Assembly[47], and the Gibson Assembly Master Mix (New England Biolabs. Ipswich, MA). Construction of the six vectors of this study were assembled in the same manner, utilizing the source vectors, pUC19 (New England Biolabs. Ipswich, MA), pTARA, pEX2000 (mchS23)[20], and pPP2000 (mchAXI-BCDEF).

Solid Media Inhibition Assays

Inhibition assays in solid media were designed and carried out based on the methods as described in Delgado et al. (2005) YojI of *Escherichia coli* functions as a microcin J25 efflux pump. *J. Bacteriol.* 187, 3465-3470, which is incorporated by reference in its entirety. Briefly, select bacterial strains were grown overnight on LB agar plates, individual colonies were selected and used to inoculate 3 mL of LB broth, and after overnight growth 1 μL of liquid culture was then used to create an agar stab in solid media and incubated at 37° C., either aerobically or anaerobically, for 24 hours. Post incubation, cells were inactivated with chloroform and UV. Molten 3% agar was then added to an overnight culture of susceptible cells to a final concentration of 0.75%, and then 3 mL of the mixture was overlaid on top of the inactivated agar stab plates and allowed to solidify. After incubation of plates in aerobic conditions overnight at 37° C. ImageJ software was utilized to quantify the area corresponding to the inhibition halo.

Purification

Briefly, cultures of *E. coli* NEB10β pHMT-I47 were grown in under antibiotic selection (ampicillin and chloramphenicol), and in iron-limiting conditions via the addition of 0.2 mM 2'2-dipyridyl, and induced with IPTG. Cultures were grown for an additional 5-7 hours post-induction, and pelleted and frozen overnight at −20° C. Cultures were then thawed in cold water, sonicated, and the crude lysate was passed through an amylose resin (New England Biolabs, Ipswich, Mass) column to capture the MBP fusion proteins, then finally eluted with maltose.

Elution was performed by adding the elution buffer (200 mM NaCl, 20 mM Tris-HCl, 10 mM maltose; pH 7.5). The eluent was concentrated using MilliporeSigma (Burlington, MA) MWCO 10,000 filters.

The concentrated MBP-MccI47 was digested by Tobacco etch virus nuclear-inclusion-a endopeptidase (TEV) (New England Biolabs, Ipswich, MA), yielding a buffered solution of MccI47, TEV, and MBP. This solution was then further purified by subsequent rounds of resuspension with Ni-NTA agarose resin (Qiagen, Hilden, DE). Ni-NTA slurry was pelleted by centrifugation and the supernatant was carefully removed by pipetting.

Results

One objective of this research is to generate vectors and strains capable of producing microcins to eradicate multidrug resistant (MDR) Enterobacteriaceae. The most obvious mode of delivery would be to orally provide the antibiotic peptide in a purified form. While this benefits from being a conventional standard and potentially more accepted by an end consumer, it is perhaps more plausible that the microcin will be more effectively delivered via a live engineered probiotic strain, directly to the site of need (gastrointestinal tract). However, before progressing towards transformation of these strains with a particular plasmid capable of microcin production, the best subset of genes of the mch cluster in order to most effectively inhibit select targets should be determined. This was performed by testing their activity in the common lab strain, *E. coli* strain NEB10β.

A series of twelve vectors were designed and constructed using a combination of PCR and Gibson Assembly, and were built as three different backbone sets, producing each of the three microcins in isolation, as well as a fourth set that expressed all three microcins from a single operon. The three different plasmid backbones were termed pBBAD, pS4BAD, and pJBAD, where pBBAD vectors contain the essential and recommended genes for microcin production: mchACDEF pS4BAD vectors are pBBAD with the addition of mchS4, and pJBAD vectors are pBBAD with the addition of mchS4 and mchS1. However, while all twelve vectors were constructed and tested, only the data pertaining the MccH47 and MccI47 are within the scope of this report, and therefore any data regarding MccM and MccIMHo is summarized in FIGS. 4A-4D. A schematic demonstrating the modular vector design of the six L-arabinose inducible MccH47/MccI47 production vectors can be seen in FIG. 2.

The $P_{BAD}$ promoter chosen and utilized for expression of the genes that code for the structural peptide and immunity protein is currently in use in clinical trials with the engineered EcN to treat phenylketonuria. The EcN can also include an fnr operator region to prevent heterologous expression in aerobic environments, providing an additional safety measure.

Strains of *E. coli* NEB10β were transformed with the six vectors discussed above and demonstrated in FIG. 3.2, and a seventh was transformed with pUC19 to serve as a negative control. Numbers were assigned to the strains based on the vector harbored: 1.) pBBAD-H47, 2.) pS4BAD-H47, 3.) pJBAD-H47, 4.) pBBAD-I47, 5.) pS4BAD-I47, 6.) pJBAD-I47, and 7.) pUC19. Static inhibition assays were performed by stabbing each strain individually into LB agar supplemented with 0.2 mM 2,2'-dipyridyl, 0.4% L-arabinose, and 100 μg/mL ampicillin, following methods described previously, and allowed to incubate overnight prior to inactivation by chloroform and UV. In this manner, the inhibitory activity of all six vectors can be evaluated against an array of target strains, where each target strain requires a single Petri dish, as can be seen in FIGS. 3A-3H. Because plates were supplemented with 100 μg/mL ampicillin to select for retention of microcin production vectors, strains lacking known mechanisms for ampicillin resistance were transformed with pUC19 (*E. coli* DH5α, *S. typhimurium* 29630, and *K. oxytoca* 700324). All other strains utilized in FIGS. 3A-3H are MDR organisms with resistance to beta-lactam antibiotics, although it is immediately apparent that ESBL-*E. coli* BAA-196 (FIG. 3B) was not resistant to ampicillin at the concentration these assays were performed, yet the interesting dynamics of this experiment justifies its retention as a part of FIGS. 3A-3H and its discussion in detail, below. Strain seven behaved as expected for a negative control and did not exhibit antimicrobial activity in all cases.

For all assays of FIGS. 3A-3H, strains harboring pBBAD-I47 (shown as strain 4 in the figures) appear to have greater activity against susceptible targets (A, B, C, G, H) than strains harboring either pS4BAD-I47 (shown as strain 5 in the figures) or pJBAD-I47 (shown as strain 6 in the figures). This contrasts MccH47 producing strains, where activity levels are most commonly strongest in pS4BAD-H47 (shown as strain 2 in the figures), followed by pBBAD-H47 (shown as strain 1 in the figures), and pJBAD-H47 with visible activity only against *E. coli* DH5αpUC19 (A), *E. coli* BAA-196 (B), and *S. typhimurium* 26930 (C).

Additionally, purifications of MccI47 were obtained and tested against an array of bacterial targets. The minimum inhibitory concentrations (MICs) for MccI47 are shown in Table 1.

TABLE 1

Minimum Inhibitory Concentrations (MICs) of bacterial strains producing MccI47

| Bacterial species | Strain | Origin | MIC (μg/ml) |
|---|---|---|---|
| *Acinetobacter baumannii** | BAA-1790 | Human clinical isolate (sputum) | ND (>138.75) |
| *Enterobacter cloacae** | BAA-2341 | Human clinical isolate | 137.38 |
| *Escherichia coli* | 25922 | Human clinical isolate | 1.58 |
| *Escherichia coli** | BAA-196 | Human clinical isolate | 4.43 |
| *Escherichia coli* | DH5α | Laboratory | 2.26 |
| *Klebsiella oxytoca** | 51983 | Human clinical isolate (blood) | ND (>197.25) |
| *Klebsiella oxytoca* | 700324 | Human isolate (bioMérieux, Inc) | ND (>197.25) |
| *Klebsiella pneumoniae** | BAA-1705 | Human clinical isolate (urine) | 36.13 |
| *Klebsiella pneumoniae** | BAA-2146 | Human clinical isolate | 29.44 |
| *Klebsiella pneumoniae** | BAA-2342 | Human clinical isolate | 16.39 |
| *Klebsiella pneumoniae** | BAA-2524 | Human clinical isolate | 14.72 |
| *Proteus mirabilis* | 29906 | Human clinical isolate (urogenital) | ND (>197.25) |
| *Pseudomonas aeruginosa* | PA14 | Human clinical isolate | ND (>138.75) |
| *Salmonella Typhimurium* | 19585 | Derived from LT2 (natural source) | 7.96 |
| *Salmonella Typhimurium* | 29630 | Derived from LT2 (natural source) | 6.31 |
| *Salmonella Typhimurium** | BAA-190 | Human clinical isolate | 12.63 |
| *Salmonella Typhi* | 700931 | Derived from TY2 (Human isolate) | 8.67 |
| *Serratia marcescens* | DB11 | Derived from DB10 (*Drosophila*) | 107.00 |
| *Shigella flexneri* | 2457T | Human clinical isolate | 0.42 |
| *Shigella flexneri* | M90T | Human clinical isolate | 0.42 |
| *Staphylococcus aureus* | 27661 | Human isolate | ND (>197.25) |

*multidrug-resistant isolate;
ND = not determined, as MIC is higher than denoted concentration Reported values are the median of at least three individual assays with each strain listed in Table 1. All tested strains of *K. pneumoniae, Salmonella, Shigella,* and *E. coli,* including many multi-drug resistant clinical isolates, were strongly inhibited by MccI47. One strain each of *Serratia marcescens* and *Enterobacter cloacae* were also inhibited. No inhibitory activity against *Acinetobacter baumannii, K. oxytoca, Proteus mirabilis, Pseudomonas aeruginosa,* or *Staphylococcus aureus* was detected with the used concentrations. This data represents the first demonstration of the inhibitory capability of purified MccI47.

Notably, MccI47 has potent activity against both MDR *K. pneumoniae* targets. In addition, it is likely that enterobactins function antagonistically and compete for receptor sites on target organisms. It may also be concluded that Class IIb microcins do not act additively, but rather compete for entry sites on target organisms, and therefore act antagonistically when supplied in conjunction.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A genetically engineered microorganism capable of producing functional microcin 147 that can inhibit the growth of bacteria, wherein the microorganism comprises a first microcin operon, a first controllable promoter for the first microcin operon, a second microcin operon, and a second controllable promoter for the second microcin operon;

wherein the first microcin operon comprises microcin genes mciI, mciA, mchC, mchD, mchE, and mchF, but not mchS1 or mchS4, wherein the first controllable promoter controls a level of expression of at least one of the microcin genes, thereby controlling an amount of microcin produced by the genetically engineered microorganism, wherein the second microcin operon comprises microcin gene mchA, and wherein the second controllable promoter controls a level of expression of the mchA gene, thereby controlling an amount of microcin produced by the genetically engineered microorganism, wherein either or both of the first microcin operon and the first controllable promoter are heterologous to the microorganism, and wherein the functional microcin I47 inhibits one or more of Klebsiella, Salmonella, Shigella, and Escherichia.

2. The genetically engineered microorganism of claim 1, wherein the genetically engineered microorganism is a bacterium.

3. The genetically engineered microorganism of claim 1, wherein the genetically engineered microorganism is Escherichia coli.

4. The genetically engineered microorganism of claim 1, wherein the first controllable promoter is, the second controllable promoter is, or both the first and the second controllable promoters are a pJ23119 promoter.

5. The genetically engineered microorganism of claim 1, wherein the first microcin operon and the first controllable promoter, or the second microcin operon and the second controllable promoter, or both the first microcin operon and the first controllable promoter and the second microcin operon and the second controllable promoter, are in the genome of the microorganism.

6. The genetically engineered microorganism of claim 1, wherein the first microcin operon and the first controllable promoter, or the second microcin operon and the second controllable promoter, or both the first microcin operon and the first controllable promoter and the second microcin operon and the second controllable promoter, are in a vector.

7. A composition that inhibits a gram-negative bacterial infection, wherein the composition comprises the genetically engineered microorganism of claim 1.

8. The composition of claim 7, wherein the composition is packaged in a capsule for intestinal delivery.

9. The composition of claim 7, wherein the bacterial infection is one or more of a Klebsiella infection, E. coli infection, Salmonella infection, and Shigella infection.

10. A method of treating intestinal dysbiosis, the method comprising:

identifying a subject as having intestinal dysbiosis; and administering to the subject a therapeutically effective amount of a composition comprising the genetically engineered microorganism of claim 1.

11. The method of claim 10, wherein the subject is a human and the composition is administered by endoscopy, enteroscopy, colonoscopy, a nasoduodenal catheter, enema, or by oral administration.

12. The method of claim 11, wherein the composition is orally administered, optionally in a capsule.

13. A method of inhibiting a gram-negative bacterial infection, the method comprising:

identifying a subject as having a bacterial infection; and administering to the subject a therapeutically effective amount of a composition comprising the genetically engineered microorganism of claim 1.

14. The method of claim 13, wherein the subject is a human and the composition is administered by endoscopy, enteroscopy, colonoscopy, a nasoduodenal catheter, enema, or by oral administration.

15. The method of claim 13, wherein the composition is orally administered, optionally in a capsule.

16. The method of claim 13, wherein the bacterial infection is a *Klebsiella* infection, *E. coli* infection, *Salmonella* infection, or *Shigella* infection.

17. A method of reducing a risk of a bacterial infection, the method comprising:

identifying a subject as having a risk of a bacterial infection; and administering to the subject a composition comprising the genetically engineered microorganism of claim 1.

18. The method of claim 17, wherein the subject has been administered one or more antibiotics prior to administration of the genetically engineered microorganism.

19. The method of claim 17, wherein the subject is a human and the composition is administered by endoscopy, enteroscopy, colonoscopy, a nasoduodenal catheter, enema, or by oral administration.

20. The method of claim 17, wherein the composition is orally administered, optionally in a capsule.

\* \* \* \* \*

SEQUENCE LISTING

<160> NUMBER OF SEQ ID NOS: 15

<210> SEQ ID NO 1
<211> LENGTH: 1119
<212> TYPE: DNA
<213> ORGANISM: Escherichia coli

<400> SEQUENCE: 1

```
atgcgaaaac gtattctttt tattggccca ccgctgtacg gtttgttata cccattgatt      60
tctctggctc aggcctttcg tgtaatcgga catgatgtag taattagtag tgctggcaaa     120
ttcgcgaata aagcagcaga agctggactg gttgtttttg atgcagttcc aggtttagat     180
tcagaggctg gatatcgcca tcaggaagag ttgaggaaaa aaagtaatat tattggtcat     240
ttctcttttt ttagcgatga aatggcagat aacctcatcg attttgcagg aaaatggagg     300
ccagatttaa tagtctatcc cccgcttggt ccggcaggcc cattggttgc tgctaaatat     360
agaattcctt cagtgatgct ggctgttgga ttcgcgcata catctgccca tattcagatg     420
ttaaaccgtt ctttaagcaa tgcttacagg cggcatggag tcagcggtcc actatgtgat     480
ttagcatgga ttgatgttgc tcccccaagt atgagcattc ttaaaaatgc tgaagaaccg     540
```

-continued

```
gttatctcaa tgagatatat tccttataac ggaggtgctg taaaggaaac atggtgggac        600
agggattctg atcgaaaacg tttactcatc agccttggca ctgtaaaacc aatggttgat        660
ggtctggagc tgatttcatg ggttatggat tctgcaaatg aagttgatgc tgatatcatt        720
ttgcaacttg caataaatgc tcgtactgga ttacgaaaac taccatcaaa tgtacgtctg        780
gttgactgga tacctatggg tgtattcctt aatggagctg atggatttat tcatcatggt        840
ggcgcaggta ataccctgac agcgttgtat agtgggatac cacagattgt gtttggcgaa        900
ggtgcagatc gctctgttaa tgcagaaatt gttgcgatgc gtgggtgtgg gattattccg        960
gacaagcatg gactgaccag tgatttggta aatcgcctgc tttatgatga ttcactacgc       1020
ttctgttcag atcaggtagc cgctgaaatg gctgaacaac ccagtcctgc agagatcgca       1080
gaggttttga tgagaaaatt aaaaaacaac gggaaataa                              1119
```

<210> SEQ ID NO 2
<211> LENGTH: 1551
<212> TYPE: DNA
<213> ORGANISM: Escherichia coli

<400> SEQUENCE: 2

```
atgagtcatc agtgttcact ttctgaactg aatgaaaacc tggtgccttt cactgccagg         60
cagatcaagt cctcattaat ctggtgtgca gaggatgtca gaaatccagg cgagctgcaa        120
aatgcctgca gttatattat cgatcctgac agtacggctt ctgccaaagt gttccatgca        180
gagcgctatg gtggcagtgg tattcagcgt aatggaggtg gtgcacgttg tgggtttgat        240
ggtaactacc aggttaaagg aataggaagt aatccgttgg ttggtgaagg tactgacgaa        300
cgtcattcta tggtgcact cggcgctgtt catgcaatat atgaggcttt gtggggagaa        360
gtactggctc aaatattacc ttatagtgct gtgcgggttc gggcggtttt acttacagat        420
ctctatactg aaaaggcatt tgagcgctcc ggtatgaaat cacgaagagc cctgttggta        480
cgtgagcctg ttgttcgccc ggcgcatttt gaacgggcac catacttcca agtaaaaccg        540
gagtattcca gtcagttaat tcacgatgcc tgtcgggtta gatctgtgat ccacaagctg        600
ccaggatatc tacctgtacc accggaagaa attgatgctg aagcacgaac tgatccccgg        660
atttattgca ttgagggatt atgtgaactg gcacgtcgtg aggcctggca aatggcattt        720
tgtcgaacac gtttcctgag attgacaact tctccttcta atattgcaat ggatggcaga        780
ttaatggatt ttaacggact cagttgctcg tttccgggag attccccagc tgattttggg        840
tataaactaa gattagctga actggcaaaa gaaccgatgg tacttatgca agggctgtct        900
gatctctgct tgtatatcgg aaaatatatg tttgaccctg acttcactct tgcagcccgt        960
ttgaaggttg aggagatatt tcagaaaact tttcatgaag catgttatta ctgttatcta       1020
gaactgttgg gtattcctgg agaatttata acacaaaaag agatacctga tatattgaaa       1080
caactggtta acagttttgt tgcattactc aataaatact gcgagaaatc acatgcccaa       1140
gatattgtca atcaggatgg ttcaccattg caaaagttgg ttgtgacgct aatccatcat       1200
aggcataatc aaaagcaggc actgaatagt agcatcaaga atgatgttta tttcaccgtt       1260
gcacaacagt gttttccca gactatccac tggctgacgc aaggcagtac cagacgtcag       1320
ataaatgctt cattactcct gaaagaaatt gaacatcata ccatgaaaag gctgcaaccc       1380
agggaagagc tgaggaaaga gaatatgtgc gaaaaaattg ccatcctgct ggataatcat       1440
ggcgatgatc ccctttttttt acaagaagca atttctgata tgaaaaattt tatgcttaag       1500 tttttccagag atgcatttgg atatcttgaa ccgataagaa acacagtgta a               1551
```

<210> SEQ ID NO 3
<211> LENGTH: 453
<212> TYPE: DNA
<213> ORGANISM: Escherichia coli

<400> SEQUENCE: 3

```
atgtcttata taagggaaac catcagagga aaagatgaat ggactgttta tgaacagata      60
ggttttgcgg tcagttgtat gctctacaat cgtaattaca gtctgtatcc ggtgttaacc     120
attcaatact ggactgaata tgcgatacag cataatcaga ttaaattcct gtttgattca     180
cgaggttttc cactggcgta tataacctgg gcatatcttg aggctgatac ggaagcgcgc     240
ctgctcaggg atccagaatt caggttgcat ccgtctgaat ggaatgaaga tggaaggatc     300
tggatcctgg atttctgttg taaaccaggc tttggtcgaa aagttattga ctatctcata     360
cagcttcagc catgggggga aggagaagta cgatggttaa gcaggcgaaa gaaaattgtg     420
acatacatcc ctgagcggct gcataaaacg tag                                   453
```

<210> SEQ ID NO 4
<211> LENGTH: 228
<212> TYPE: DNA
<213> ORGANISM: Escherichia coli

<400> SEQUENCE: 4

```
atgcgagaaa taacagaatc acagttaaga tatatttccg gggcgggagg tgcgccagcg      60
acttcagcta atgccgcagg tgctgcagct attgttggag ctctcgccgg aatacctggt     120
ggtccacttg gggttgtagt tggagccgta tctgccggtt tgacaacagc aattggctcg     180
accgtgggaa gtggtagtgc cagttcttct gctggtggcg gtagctaa                  228
```

<210> SEQ ID NO 5
<211> LENGTH: 1275
<212> TYPE: DNA
<213> ORGANISM: Escherichia coli

<400> SEQUENCE: 5

```
ttgtttcgtc aggatgcttt agaaaacaga aaaatgaagt ggcagggacg ggcaatatta      60
cttcccggaa taccactatg gttaatcatg ctgggaagca ttgtgtttat tacggcattt     120
ctgatgttca ttattgttgg tacctatagc cgccgtgtta atgtcagtgg tgaggtcaca     180
acctggccaa gagctgtcaa tatatattca ggtgtacagg gatttgttgt caggcaattt     240
gttcatgaag ggcagttgat aaaaaaaggg gatcctgttt atctgattga catcagtaaa     300
agtacacgta gtggtattgt cactgataat catcggcggg atatagaaaa tcagctggtt     360
cgtgtggaca acattatttc ccgtctggaa gaaagtaaaa aaataacgtt agataccctg     420
gaaaaacaac gtctgcaata cacagatgcg tttcgtcgct catcagatat tatacagcgt     480
gcagaggaag ggataaaaat aatgaaaaac aatatggaga attacagaaa ctatcaggca     540
aaagggctga ttaataaaga tcagttaact aaccaggtgg cattatatta tcagcaacaa     600
aacaatcttc tcagcctgag cggacagaac gaacagaatg ccctgcagat aaccactctg     660
gagagtcaga ttcagactca ggctgcagat tttgataacc gtatctacca gatggaactg     720
caacggtacg agttacagaa agaactggtt aacactgatg tggagggcga aattattatc     780
cgggcgttga ctgacgggaa agttgactcc ctgagtgtca ctgtcgggca aatggtcaat     840
accggagaca gccttctgca ggttattcct gagaacattg aaaactatta tcttattctc     900
```

-continued

```
tgggtcccaa atgatgctgt tccttatatt tcggctggtg acaaagtgaa tattcgttat      960
gaagcctttc cggcagaaaa atttgggcag ttctctgcta cggttaaaac tatatccagg     1020
actcctgcgt caacacagga aatgttgacc tataagggtg caccacagaa tacgccgggc     1080
gcctctgttc cctggtataa agtcattgcg atgcctgaaa agcagattat cagatatgac     1140
gaaaaatacc tccctctgga aaatggaatg aaagccgaaa gtacactatt tctggaaaaa     1200
aggcgtattt accagtggat gctttctcct ttctatgaca tgaaacacag tgcaacagga     1260
ccgctcaatg actaa                                                       1275

<210> SEQ ID NO 6
<211> LENGTH: 2097
<212> TYPE: DNA
<213> ORGANISM: Escherichia coli

<400> SEQUENCE: 6
atgactaacg ggagtttcag acaaattata aatcagcttg atatgcgctg gcgacgtcgt       60
gttccggtta ttcatcagac ggagaccgct gaatgtggac tggcctgcct ggcaatgata      120
tgcggtcatt ttggtaagaa tattgacctg atatctcttc gccggaagtt taatctctcg      180
gcccgtggag caaaccttgc aggaatcaat ggaatagcgg agcagctggg gatggtcacc      240
cgggctcttt cactggagct ggatgaactt ggtgccctca aaatgccgtg tattctccac      300
tgggatttca gtcactttgt cgtgctggtc agcgtaaagc gtaaccgtta tgtactgcat      360
gatccggcca gaggcagaag atatctcggt cgggaggaaa tgagccggta ttttacgggc      420
attgcacttg aggtctggcc tggaagtgaa ttcctggcgg aaacccagca gatccgcata      480
agtctccgtt cactgattaa cagtatttac ggtattaaaa gaacactggc gaaaattttc      540
tgtctgtcag ttgtaattga agcaatcaat ctggtaatgc cggtggggac tcagctggtt      600
atggatcatg cgattccggc gggggacaga gggctgctga cgcttatttc tgctggcctg      660
atgttcttta tattgctcag ggccgcggtg agtatgctgc gtgcatggtc ctcactggtt      720
atgagcacgc tcatcaatat acagtggcag tcgggtctgt ttaaccatct tctcagactg      780
ccgctggcgt tttttgaacg ccgtaaatta ggtgatatcc agtcgcgttt tggctccctt      840
gacactttga gggccacctt taccacctgt gtggttgggg caatcatgga cagtattatg      900
gttgtggggg tttttgtgat gatgctgtta tatggaggat atcttacctg ataagtgctc      960
ggttttacca tggtttacgt tcttattcgt ctggtgacat acggctatta ccggcaaata     1020
tcggaagaaa ctcttgtcag gggggcccgg gccagctcct attttatgga aagcctgtat     1080
ggtattgcca cggtaaaaat ccaaggtatg gctgggatcc ggggaacaca ctggcttaac     1140
ctgaaaatag atgcgatcaa ttcaggtatt aagttaacca gatgggattt gctcttcggg     1200 gggataaaata cttttgttgc cgcctgtgat caggtggcga ttttatggct gggtgcaagc     1260
cttgtgatcg ataatcagat gacaataggg atgtttgtgg catttggttc ttttcgtggg     1320
cagttttcgg atcgggttgc ttcgctgacc agttttcttc ttcaactgag aataatgagt     1380
ctgcataatg agcgcattgc agatattgca ctacatgaaa aggaagaaaa gaaaccggaa     1440
attgaaatcg ttgctgacat gagcccggtt tcactggaaa ccactgattt aagctaccgg     1500
tatgacagcc agtcagcaca ggtattcagt ggtctgaatt tgtctgtggc tccgggagaa     1560
agtgtggcta taactggtgc ctccggtgcc ggaaaaacca cattaatgaa agtattatgt     1620
ggactgtttg aaccagatag tggaaaagta ctggttaatg gcacggatat acgtcaactt     1680
ggaataaata attatcaccg tatgatagcc tgtgttatgc aggacgaccg gctattttca     1740
```

-continued

```
ggatcaattc gtgaaaatat ctgtgggttt gcagaagaaa cagacgacga atggatgaca      1800
gaatgtgcca gagcaagtca tattcatgat gtgataatga aaatgccaat ggggtatgaa      1860
acgttaatag gtgaactggg ggaaggtctt tccggcggtc aaaaacagcg tatattcatt      1920
gcccgagctt tataccggaa acctggaata ttatttatgg atgaggctac aagttctctt      1980
gatacagaaa gtgaacgttt cgtgaatgct gccataaaaa aaatgaatat cacccgggtg      2040
attattgcac acagagaaac tacgttgaga actgttgaca ggattatttc tatttaa        2097

<210> SEQ ID NO 7
<211> LENGTH: 210
<212> TYPE: DNA
<213> ORGANISM: Escherichia coli

<400> SEQUENCE: 7
atgagttata aaaaactgta ccaattgacg gctatattta gtttacctct tactatctta        60
ttggtttcac tttcatccct tcggattgtt ggcgaaggga attcttatgt tgacgttttt       120
ctaagcttta taatatttct tggttttatt gagctgattc atgggattcg aaagattttg       180
gtctggtcag gctggaaaaa cggaagttaa                                        210

<210> SEQ ID NO 8
<211> LENGTH: 120
<212> TYPE: DNA
<213> ORGANISM: Escherichia coli

<400> SEQUENCE: 8
atggaatttg ctacaaacag ggttactgta aatgacagtc ggtcagcact gtcatcaact        60
ttgctgttgt ctttgatcat gagcgccact ctactggaat attctttatc gatgacctga       120

<210> SEQ ID NO 9
<211> LENGTH: 1266
<212> TYPE: DNA
<213> ORGANISM: Escherichia coli

<400> SEQUENCE: 9
atgaaaaact atcttttcca gactcccgaa gatatttgtg tacagttaaa aaaaatgaca        60
catcctgtca caataagaac aacagatatt gctaatttct ggcactatct tgagtcagca       120
actcttccgg tgatcacaaa aagcaccact acagaaaatc gggaggttac atttctgtgg       180
cgctcagaga aagcagtgca aggcgtatat cttcgcctga atcgtgttac agataaaaaa       240
gatgtcaaaa aaggactaat gactcatatc ccttcgacag atatctggat gctgacactg       300
gtgttaccag cttcatatcg gggctcatac tcatttatag aaattcccac agatatgaca       360
caaaaagaca tatttcaact aggaagtcgc ttctctccat tacccggtaa atctgatcca       420
tttaacaaaa cagcagaaat aaatatacga ggattcggag aatcagtcct ttctcttgat       480
atggctcctg aacaaaagga atgggatgat acttcccata aatgtacagg tattctttca       540
acattacatt cctttgttgc aggatatcaa cgccggattc gtttatattt tccccagaat       600
ccaacatcag tacctcttgg attacttgtg ttacctgatg ctgaaatatg gtttgaccgg       660
atggatatta cccgggcatt agatatggcc attaccactg gtcatattgc gccaatggca       720
attatgggga tagacaatat taatgaatct gatcgtatga atatactggg aggcaataaa       780
gaacttatct ttgatatagc ggaaaatctg atacccagt tatacagaga ctacccgaat       840
atcgtatggg ctggtcgttc taatactata ctggccggtc agagcctcgg tggagtgaca       900
```

-continued

```
gcactgatgg cagctatata tgcgtcgaca acatttggta caatcattag ccactcacct      960
tcaatgtggt ggaaccctga ccagggcagc ccgattttgt ttactgagaa tgatatctcc     1020
tgggtaagtg agcagatact ttcagcgcct ccgaaagatg taaatatcca acttggagtc     1080
ggttctttag aaggtacaac cgtctcacat gttcagcggt tgcatcagtc gttaatcgca     1140
gcaggtttgg aaagtaacct cactgtctat gccggtggtc atgattatgc ctggtggcgc     1200
ggagcaatta ttgatgcatt agcaaattat aattgcagga agatatcaga taataacttt     1260
gtgtaa                                                                 1266

<210> SEQ ID NO 10
<211> LENGTH: 246
<212> TYPE: DNA
<213> ORGANISM: Escherichia coli

<400> SEQUENCE: 10
atgaattgtg ataataatca cagaaatgaa gaattcattg ttacctttga taaaggcaac       60
aagcaagaca attcaagacg aaaacacgat aattttccta tagaggtaga atcctccgta      120
gagctggaga cacactgtat cacaaataat aagtcggctt ccggtatagt aacacatgac      180
tatgatgccg attatatttg tggttgtggt gaaattatgt gtcctggttg cggtcatgac      240
ctataa                                                                 246

<210> SEQ ID NO 11
<211> LENGTH: 234
<212> TYPE: DNA
<213> ORGANISM: Escherichia coli

<400> SEQUENCE: 11
atgagagaaa tatcagataa catgcttgat tccgtgaaag gagggatgaa tcttaatgga       60
ttacctgctt ctactaatgt aatagatcta cgtggaaaag atatgggaac atatattgat      120
gctaatggag catgctgggc tccggatact ccatccatca tcatgtatcc ggggggaagt      180
ggaccttctt atagtatgag tagttccaca tccagtgcaa acagcggcag ttaa             234

<210> SEQ ID NO 12
<211> LENGTH: 435
<212> TYPE: DNA
<213> ORGANISM: Escherichia coli

<400> SEQUENCE: 12
atgtatctta cgaaaaagat tataataagt atgatgttta tattaccatc tgctgcattt       60
tcatcagatc cacctcccct tcaacaatcg ttagaaaaaa caacctattt ttctataggt      120
atgaatgggt ttataggcta tcagagcgaa ggggaaaaat tatacacaca cattcttaca      180
ttagataatc ccgaagagat atttaaaaat ataataaaaa atagaaagtc aactaaggag      240
tctaaaattt atgctgcttg tgggctatat tatttaaacg tagaaaatat agagtcattg      300
tttaatgaaa atgataaaca agaatatgtg tctgtcttaa gagggggatat tttaacaaaa      360 ataaaactga atgatattct gaattctgtg ataataaatg gttgcaacac caaattaata      420
tctgaacata aatga                                                       435

<210> SEQ ID NO 13
<211> LENGTH: 122
<212> TYPE: DNA
<213> ORGANISM: Artificial
<220> FEATURE:
<223> OTHER INFORMATION: pBAD promoter sequence
```

-continued

```
<400> SEQUENCE: 13
ccacaattca gcaaattgtg aacatcatca cgttcatctt tccctggttg ccaatggccc       60
attttcctgt cagtaacgag aaggtcgcgt attcaggcgc tttttagact ggtcgtaatg      120
aa                                                                     122

<210> SEQ ID NO 14
<211> LENGTH: 163
<212> TYPE: DNA
<213> ORGANISM: Artificial
<220> FEATURE:
<223> OTHER INFORMATION: Pttr promoter sequence

<400> SEQUENCE: 14
cccaatatcc ctgtcaatta tgttgtttta gatcaacaac aagccgggta tgtggttaac       60
cacaatagag cgcaccccgc ctcgattttt acactgtaaa tcatcgacat tttttattca      120
ttacacatga accaacatcg tgacaaatgt ttcattgttg gca                        163

<210> SEQ ID NO 15
<211> LENGTH: 34
<212> TYPE: DNA
<213> ORGANISM: Artificial
<220> FEATURE:
<223> OTHER INFORMATION: J23119 promoter sequence

<400> SEQUENCE: 15
ttgacagcta gctcagtcct aggtataatg ctag                                   34
```